United States Patent [19]

Mathews et al.

[11] Patent Number: 5,786,302

[45] Date of Patent: Jul. 28, 1998

[54] HERBICIDAL METHOD USING SUBSTITUTED PYRAZOLE COMPOUNDS

[75] Inventors: Christopher John Mathews, Pinole; Don Robert Baker, Orinda, both of Calif.

[73] Assignee: Zeneca Limited, London, England

[21] Appl. No.: 905,749

[22] Filed: Aug. 4, 1997

Related U.S. Application Data

[60] Provisional application No. 60/019,403, Nov. 15, 1995.

[62] Division of Ser. No. 742,010, Oct. 31, 1996, Pat. No. 5,698,495.

[51] Int. Cl.⁶ ................................................. A01N 43/56
[52] U.S. Cl. ................... 504/282; 548/364.1; 548/365.7; 548/366.1
[58] Field of Search ............................................... 504/282

[56] References Cited

U.S. PATENT DOCUMENTS 4,008,249  2/1977  Fischer et al. .

FOREIGN PATENT DOCUMENTS 0 177 710A   4/1986   European Pat. Off. .
36 02 379    7/1987   Germany .
08245594A    9/1996   Japan .

*Primary Examiner*—Robert W. Ramsuer
*Attorney, Agent, or Firm*—Melissa A. Shaw

[57] ABSTRACT

Herbicidal compositions containing substituted pyrazole compounds and derivatives thereof of the formula:

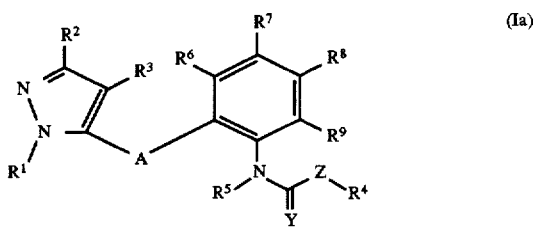

wherein Y and O or S is Z is a carbon-carbon single bond, O, S, C=O or C=N. Methods of controlling undesirable vegetation using these compounds and derivatives are also disclosed. Herbicidal compounds wherein Z is a carbon-carbon single bond, S, C=O or C=N are also described.

4 Claims, No Drawings

HERBICIDAL METHOD USING SUBSTITUTED PYRAZOLE COMPOUNDS

This application is a divisional of application number 08/742,010, filed Oct. 31, 1996 now U.S. Pat. No. 5,695,495, which in turn claims the benefit of U.S. provisional application number 60/019,403, filed Nov. 15, 1995.

FIELD OF THE INVENTION

In one aspect, this invention relates to novel substituted pyrazole compounds and derivatives thereof which exhibit unexpectedly desirable herbicidal activity. In other aspects, this invention relates to herbicidal compositions containing a substituted pyrazole compound or derivative thereof and an agriculturally acceptable carrier and to a method of controlling undesirable vegetation by applying to an area where control is desired an herbicidally effective amount of a substituted pyrazole compound or derivative thereof

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on non-cropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide novel herbicidal compositions and novel methods of controlling weeds.

SUMMARY OF THE INVENTION

In one aspect, this invention is directed to compounds of formula (I):

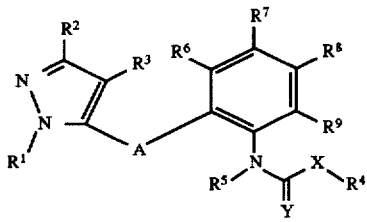

(I)

wherein:

$R^1$ is optionally substituted $C_1$–$C_6$ alkyl or $C_1$–$C_6$ haloalkyl;

$R^2$ is optionally substituted $C_1$–$C_6$ alkyl, $C_1$–$C_6$ haloalkyl or $C_3$–$C_6$ cycloalkyl;

$R^3$ is hydrogen, halogen, $C_1$–$C_6$ alkyl or $C_1$–$C_6$ haloalkyl;

$R^4$ is optionally substituted $C_1$–$C_6$ alkyl, $C_1$–$C_6$ haloalkyl, optionally substituted $C_1$–$C_6$ alkoxy, optionally substituted $C_3$–$C_6$ cycloalkyl, optionally substituted ($C_1$–$C_6$)alkoxy($C_1$–$C_6$)alkyl, optionally substituted $C_2$–$C_6$ alkenyl, optionally substituted $C_2$–$C_6$ alkynyl, optionally substituted aryl, optionally substituted heteroaryl, or an optionally substituted five or six membered heterocyclic ring containing one or more heteroatoms selected from O, N or S;

$R^5$ is hydrogen, optionally substituted $C_1$–$C_6$ alkyl or ($C_1$–$C_6$)alkoxy-($C_1$–$C_6$)alkyl;

$R^6$, $R^7$, $R^8$ and $R^9$ are independently selected from hydrogen, halogen, optionally substituted $C_1$–$C_6$ alkyl, optionally substituted $C_2$–$C_6$ alkenyl, optionally substituted $C_2$–$C_6$ alkynyl, optionally substituted $C_1$–$C_6$ alkoxy, ($C_1$–$C_6$)alkoxy-($C_1$–$C_6$)alkyl, $C_1$–$C_6$ haloalkyl, $C_1$–$C_6$ haloalkoxy, cyano, nitro, —$S(O)_p$—$R^{10}$ wherein p is 0, 1 or 2 and $R^{10}$ is $C_1$–$C_3$ alkyl or $C_1$–$C_3$ haloalkyl, —$OSO_2R^{11}$ wherein $R^{11}$ is $C_1$–$C_3$ alkyl, —$CO_2H$, —$COR^{12}$, —$COOR^{12}$ or —$NHCOR^{12}$ wherein $R^{12}$ is $C_1$–$C_6$ alkyl, $C_1$–$C_6$ haloalkyl, optionally substituted $C_3$–$C_6$ cycloalkyl, optionally substituted aryl, optionally substituted heteroaryl, ($C_1$–$C_6$) alkoxy-($C_1$–$C_6$)alkyl or $C_1$–$C_6$ alkylthio, —$CONR^{13}R^{14}$ or —$NR^{13}R^{14}$ wherein $R^{13}$ and $R^{14}$ may be the same or different and are each hydrogen, $C_1$–$C_6$ alkyl, $C_1$–$C_6$ haloalkyl, optionally substituted $C_3$–$C_6$ cycloalkyl, optionally substituted $C_2$–$C_6$ alkenyl, optionally substituted $C_2$–$C_6$ alkynyl, optionally substituted aryl, optionally substituted heteroaryl, ($C_1$–$C_6$)alkoxy-($C_1$–$C_6$)alkyl or $C_1$–$C_6$ alkylthio, or $R^{13}$ and $R^{14}$ together with the N to which they are bound may form a ring having 3–8 members, one or more of which may be O, S or N; and A is O, S, SO or $SO_2$;

Y is O or S;

X is a carbon-carbon single bond, S, C=O or C=N;

and agriculturally acceptable salts thereof.

In another aspect, this invention is directed to an herbicidal composition containing (A) a compound of formula (Ia)

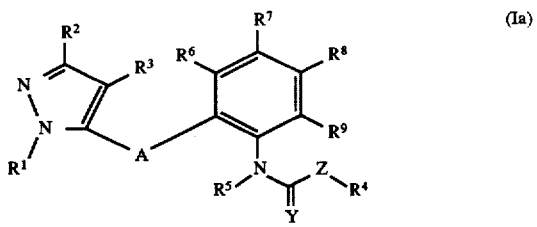

(Ia)

wherein $R^1$, $R^2$, $R^3$, $R^4$, $R^5$, $R^6$, $R^7$, $R^8$, $R^9$, A and Y have the same meanings as above and Z is a carbon-carbon single bond, O, S, C=O or C=N; or an agriculturally acceptable salt thereof; and (B) a carrier therefor.

In still another aspect, this invention is directed to a method for controlling undesirable vegetation by applying to an area where such vegetation control is desired an herbicidally effective amount of a compound of formula (Ia):

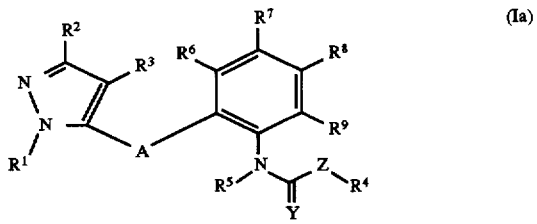

(Ia)

wherein $R^1$, $R^2$, $R^3$, $R^4$, $R^5$, $R^6$, $R^7$, $R^8$, $R^9$, A, Y and Z have the same meanings as above an agriculturally acceptable salt thereof.

DETAILED DESCRIPTION OF THE INVENTION

The novel herbicidal compounds of this invention are of the formula (I):

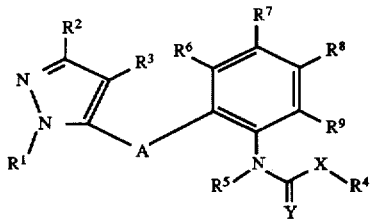

(I)

wherein $R^1$, $R^2$, $R^3$, $R^4$, $R^5$, $R^6$, $R^7$, $R^8$, $R^9$, A, Y and X have the same meanings as above; and agriculturally acceptable salts thereof.

Preferably, $R^1$ is $C_1$–$C_3$ alkyl or $C_1$–$C_3$ haloalkyl; $R^2$ is $C_1$–$C_3$ alkyl or $C_1$–$C_3$ haloalkyl; $R^3$ is hydrogen; and $R^5$ is hydrogen.

Particularly preferred compounds include: N-[4-Methyl-2-[1-methyl-3-(trifluoromethyl)-1H-pyrazol-5-yl]oxyphenyl]cyclopropane carboxamide; N- [4-Methyl-2-[1-methyl-3-(trifluoromethyl)-1H-pyrazol-5-yl]oxyphenyl] isopropane carboxamide and N-[4-Methyl-2-[1-methyl-3-(trifluoromethyl)-1H-pyrazol-5-yl]oxyphenyl]ethane carboxamide.

In another aspect, this invention is directed to a herbicidal composition containing (A) a compound of formula (Ia)

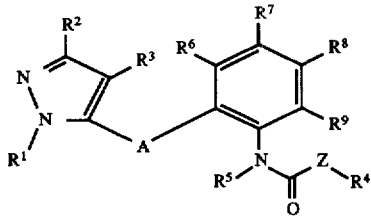

(Ia)

wherein $R^1$, $R^2$, $R^3$, $R^4$, $R^5$, $R^6$, $R^7$, $R^8$, $R^9$, A, Y and Z have the same meanings as above an agriculturally acceptable salt thereof; and (B) a carrier therefor.

In still another aspect, this invention is directed to a method for controlling undesirable vegetation by applying to an area where such vegetation control is desired an herbicidally effective amount of a compound of formula (Ia):

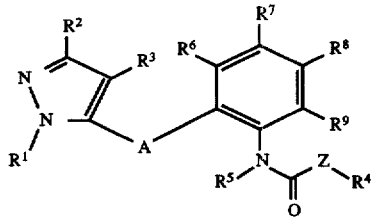

(Ia)

wherein $R^1$, $R^2$, $R^3$, $R^4$, $R^5$, $R^6$, $R^7$, $R^8$, $R^9$, A, Y and Z have the same meanings as above, or an agriculturally acceptable salt thereof.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra molecular or intermolecular hydrogen bonding, or otherwise.

As employed herein, the word "substituted" is intended to mean that the "substituted" group has one or more of the following substituents: halogen (i.e., fluorine, chlorine, bromine and iodine); $C_1$–$C_4$ alkyl; $C_1$–$C_4$ alkylthio; $C_1$–$C_4$ alkoxy; $(C_1$–$C_4)$alkoxy-$(C_1$–$C_4)$alkyl; $(C_1$–$C_6)$alkoxyCO-; $C_1$–$C_4$ alkyl-S(O)$_p$-; nitro; nitrile; cyano; carboxy and salts, amides and esters thereof; alkanoyl of 2 to 4 carbon atoms; amino optionally substituted with one or two $C_1$–$C_4$ alkyl; phenyl optionally substituted with one or more $C_1$–$C_4$ alkyl, $C_1$–$C_4$ alkoxy, $C_1$–$C_4$ alkyl-S(O)$_p$-, nitro, halogen, fluorine, chlorine, bromine, cyano, or $CF_3$ groups; a five or six membered heterocyclic ring containing one or more heteroatoms selected from O, N or S; a five or six membered heterocyclic ring containing one or more heteroatoms selected from O, N or S optionally substituted with one or more $C_1$–$C_4$ alkyl, $C_1$–$C_4$ alkoxy, $C_1$–$C_4$ alkyl-S(O)$_p$-, nitro, halogen, fluorine, chlorine, bromine, cyano, or $CF_3$ groups.

The term "optionally substituted aryl" is intended to include aryl groups, such as phenyl, which are unsubstituted or are substituted with one or more of the foregoing substituents. Similarly, the term "optionally substituted heteroaryl" is intended to include heteroaryl groups, such as pyridyl, pyrimidyl, triazinyl, thienyl, firyl and thiazolyl, which are unsubstituted or are substituted with one or more of the substituents listed above.

The expression "salts, amides and esters thereof" used above in relation to carboxy substitution includes, for example, salts formed from alkali metals (e.g., sodium, potassium and lithium), alkaline earth metals (e.g., calcium and magnesium), the ammonium ion and substituted ammonium ions wherein one, two, three or four of the hydrogen atoms have been replaced by optionally substituted $C_1$–$C_6$ hydrocarbyl moieties as defined above. Likewise, the carboxy substitution includes esters and amides which may be formed from the carboxy group and an optionally substituted $C_1$–$C_6$ hydrocarbyl moiety in the case of the ester, or an optionally substituted $C_1$–$C_6$ hydrocarbyl amine in the case of the amide.

In the above definitions, the term "halogen" includes fluoro, chloro, bromo and iodo groups. In polyhalogenated groups, the halogens may be the same or different.

The compounds of the present invention have been found to be active herbicides, possessing utility as pre-emergence and post-emergence herbicides. These compounds are useful against a wide range of plant species including broadleaf, grassy and perennial species. The compounds of this invention have also been found to be particularly effective in controlling undesirable vegetation typically found in rice crops.

The terms "herbicide" and "herbicidal" are used herein to denote the inhibitive control or modification of undesired plant growth. Inhibitive control and modification include all deviations from natural development, such as, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and aboveground portions.

The term "agriculturally acceptable salt" is easily determined by one of ordinary skill in the art and includes hydrohalide, acetic, sulfonic, phosphonic, inorganic and organic acid salts.

In general, the compounds of this invention may be prepared by treatment of an amine (II) with an acid chloride, acid anhydride, chlorothio formate, chloroformate or similar reagent in the presence of a suitable base and in a suitable solvent, according to the procedures described, for example, in J. March, *Advanced Organic Chemistry*, third edition, pp. 370–377, J. Wiley and Sons, New York (1985) and references therein. Many of these amines (II) are believed to be novel and are to be considered as yet another aspect of the present invention. Alternatively amine (II) may be treated sequentially with phosgene, or a phosgene equivalent, and an appropriate alcohol or thiol to generate (Ia) wherein $R^5$ is hydrogen. Such procedures are well known in the literature (for example see Babad, H. and Zeiler, A. G., *Chem Rev.*, 1973, 73, 75) [SCHEME 1]

SCHEME 1

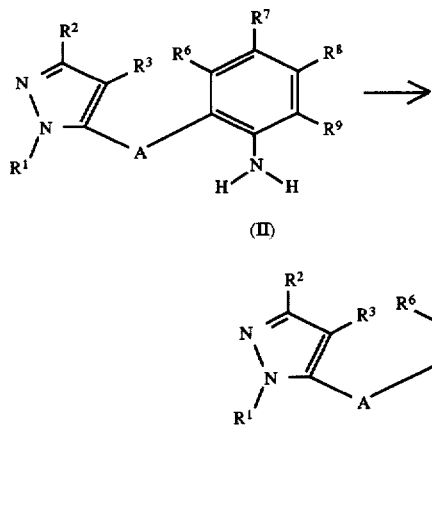

(Ia); $R^5$ = H

Compounds of formula (Ia) wherein $R^5$ is hydrogen may be converted readily into compounds of formula (Ia) wherein $R^5$ is alkyl, alkoxyalkyl etc. by treatment with a suitable base, such as an alkali metal hydride and an appropriate alkylating agent (such as an alkyl halide) in a suitable solvent. Such reactions are well known to those skilled in the art, and need no further description here.

The amine (II) may be prepared by reduction of the corresponding nitro compound (III); such reductions are widely described in the literature. Those skilled in the art will know that the reduction may be carried out using a variety of reducing agents such as hydrogen in the presence of a catalyst, sodium borohydride in the presence of a palladium catalyst, a sulfide or a metal such as iron in the presence of an acid; the particular method of choice will depend on, amongst other things, the compatibility of the reductants with other substituents present in the molecule. References to a variety of methods suitable for the reduction of aromatic nitro groups may be found in H.O. House, *Modern Synthetic Reactions*, ed. R. Breslow, W. A Benjamin Inc., New York, 1965. [SCHEME 2]

SCHEME 2

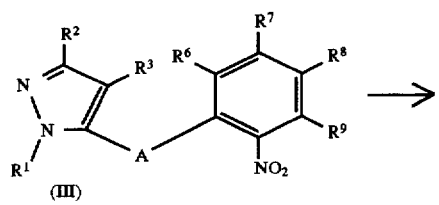

-continued
SCHEME 2

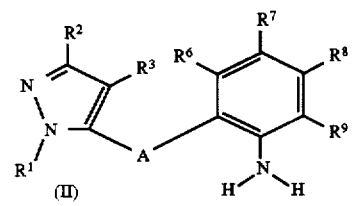

(II)

When A is oxygen, the nitrobenzene of formula (III) may be prepared by reacting a compound of type (IV), where Hal is halogen such as fluorine or chlorine, with a hydroxypyrazole (V). The reaction is preferably carried out in an organic solvent such as N,N-dimethylformamide, dimethylsulfoxide, acetonitrile, a lower alcohol or a lower alkyl ketone and in the presence of a suitable base such as an alkali metal carbonate, hydroxide or alkoxide. Moderate temperatures, for example from 0° to 100° C. are suitably employed. [SCHEME 3].

SCHEME 3

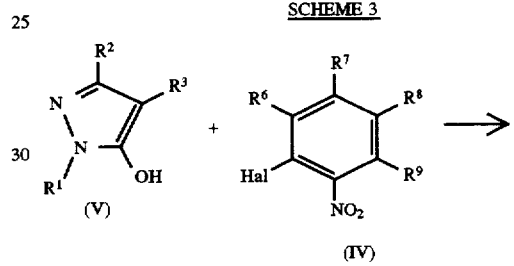

(III)

Compounds of the type (IV) are commercially available, or can be made by methods known in the literature.

Hydroxypyrazoles of the type (V) can be made by methods known in the art. Hydroxypyrazoles of the type (V), wherein $R^3$ is halogen, may be made, for example by reaction of an unsubstituted pyrazole ($R^3$ is H) with a halogenating agent such as sulfuryl chloride or N-bromosuccinimide in a suitable solvent. Compounds of the type (V), ($R^3$ is hydrogen or alkyl) may be prepared by treatment of an appropriate β-ketoester (VI) with an alkylhydrazine in a suitable solvent, as described, for example by DeStevens et al., *JACS*, 81, 6292, (1959) [SCHEME 4].

SCHEME 4

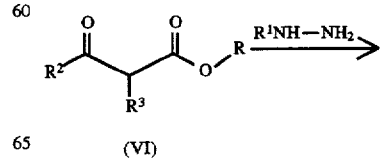

(VI)

-continued
SCHEME 4

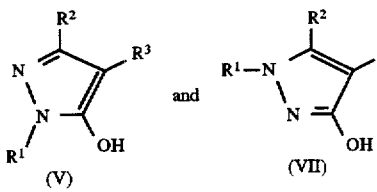

Such a procedure may produce a mixture of 5-hydroxy-(V) and 3-hydroxy-pyrazoles (VII), though normally these can be separated if desired by conventional purification techniques (see, for example, L. F. Lee et al., *J Heterocyclic Chem.*, 27, 243, [1990]).

Compounds wherein A is sulfur may be synthesized starting with compounds of formula (V). The hydroxy group at the 5-position of formula (V) is converted to its corresponding mercaptan. In a typical reaction, compounds of formula (V) are dissolved in a suitable solvent such as toluene and a stoichiometric excess of Lawesson's reagent [2,4-bis(4-methoxyphenyl)-1,3-dithia-2,4-diphosphetane-2, 4-disulfide] is added. The reaction mixture is heated to reflux and this temperature is maintained for about 10 hours. Subsequently, the reaction mixture is cooled and stirred at room temperature for about 18 hours. Next, the reaction mixture is poured into aqueous sodium carbonate, or the like, to quench the reaction. The resulting aqueous phase is acidified with a strong protic acid such as concentrated hydrochloric acid. The resulting acidic solution is worked up with conventional techniques to yield the desired mercaptan of formula (VIII).

SCHEME 5

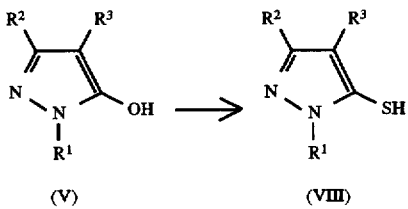

The compounds of formula VIII are treated in the same manner as compounds of formula V to produce the corresponding intermediate compound in Scheme 3, wherein the pyrazole ring is linked to the phenyl ring via a sulfur atom. This sulfur intermediate is then treated as in Schemes 2 and 1 to generate the compounds of formula I and Ia wherein A is sulfur.

The compounds of the present invention are useful as herbicides and can be applied in a variety of ways known to those skilled in the art, at various concentrations. The compounds are useful in controlling the growth of undesirable vegetation by pre-emergent or post-emergent application to the locus where control is desired. The compositions of this invention comprise a compound of formula (Ia) above and a suitable carrier, which carriers are well known to one of ordinary skill in the art.

In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of plants to be controlled. The rate of application will generally vary from about 0.01 to about 11.5 kilograms per hectare, preferably from about 0.02 to about 4.5 kilograms per hectare.

Wettable powders are in the form of finely divided particles which disperse readily in water or other liquid carriers. The particles contain the active ingredient retained in a solid matrix. Typical solid matrices include fuller's earth, kaolin clays, silicas and other readily wettable organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Microcapsules are typically droplets or solutions of the active material enclosed in an inert porous shell which allows escape of the enclosed material to the surrounds at controlled rates. Encapsulated droplets are typically about 1 to 50 microns in diameter. The enclosed material typically constitutes about 50 to 95% of the weight of the capsule, and may include solvent in addition to the active compound. Shell of membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. Benzo-2,1,3-thiadiazin-4-one-2,2-dioxides such as bentazone;

B. hormone herbicides, particularly the phenoxyalkanoic acids such as MCPA, MCPA-thioethyl, dichlorprop, 2,4,5-T, MCPB, 2,4-D,2,4-DB, mecoprop, trichlopyr, fluroxypyr, clopyralid, and their derivatives (e.g. salts, esters and amides);

C. pyrazole derivatives such as pyrazoxyfen, pyrazolate and benzofenap;

D. dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and termacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogly-cofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim and salts thereof, sethoxydim, cycloxydim, sulcotrione, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M63 13, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazathapyr;

W. arylanilide herbicides such as flamprop and esters thereof, benzoylpropethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. 4-benzoylisoxazole and 2-cyano-1,3-dione herbicides.

BB. miscellaneous herbicides including ethofumesate, cinmethylin, difenzoquat and salts thereof such as the methyl sulfate salt, clomazone, oxadiazon, bromofenoxim, barban, tridiphane, flurochloridone, quinchlorac and mefanacet; and CC. contact herbicides, examples of which include bipyridylium herbicides such as those in which the active entity is paraquat and those in which the active entity is diquat.

*These compounds are preferably employed in combination with a safener such as 2,2-dichloro-N,Ndi-2-propenylacetamide (dichlormid).

These formulations can be applied to the areas where control is desired by conventional methods. Dust and liquid compositions, for example, can be applied by the use of powerdusters, boom and hand sprayers and spray dusters. The formulations can also be applied from airplanes as a dust or a spray or by rope wick applications.

The following are examples of typical formulations:

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| Wettable powders: | |
|---|---|
| 70%: | 70 parts active compound |
| | 5 parts sodium dibutylnaphthylsulfonate |
| | 3 parts naphthalenesulfonic acid phenolsulfonic acid/phenol-sulfonic acid/formaldehyde condensate |
| (3:2:1) | |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25% | 25 parts active compound |
| | 4.5 parts calcium lignin sulfate |
| | 1.9 parts Champagne chalk/-hydroxyethyl cellulose (1:1) |
| | 8.3 parts sodium aluminum silicate |
| | 16.5 parts kieselguhr |
| | 46 parts kaolin |
| 10% | 10 parts active compound |

-continued

Wettable powders:

3 parts of a mixture of sodium salts of saturated fatty alcohol sulfates
5 parts naphthalenesulfonic acid/formaldehyde condensate
82 parts kaolin These wettable powders are prepared by intimately mixing the active compounds with the additives in suitable mixers, and grinding the resulting mixture in mills or rollers.

Emulsifiable concentrate:

25%  25 parts active substance
     2.5 parts epoxidized vegetable oil
     10 parts of an alkylarylsulfonate/fatty alcohol polyglycol ether mixture
     57.5 parts xylene The amount of the present compositions which constitute a herbicidally effective amount depends upon the nature of the seeds or plants to be controlled. The rate of application of active ingredients varies from about 0.01 to about 28 kilograms per hectare, preferably about 0.02 to about 11 kilograms per hectare with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to limit the scope of this invention in any manner whatsoever.

Example 1

N-[4-Methyl-2-[1-methyl-3-(trifluoromethyl)-1H-pyrazol-5-yl]oyphenyl-cyclopropane carboxamide Compound 1

A. Preparation of 5-hydroxy-1-methyl-3-trifluoromethylpyrazole

A. Methyl hydrazine (13.3 ml, 11.5 g, 0.25 mol) was added dropwise to a chilled (ice-bath) solution of ethyl 4,4,4-trifluoroacetoacetate (46.0 g, 0.25 mol) in toluene (250 ml) at such a rate that the temperature of the reaction could be maintained below 10° C. (ice-bath cooling). Once the addition was complete the ice-bath was removed and stirring continued at room temperature for 1 hour and then at reflux (Dean-Stark) for 3 h. The mixture was allowed to cool to room temperature and allowed to stand over 3 days. The precipitate was collected by filtration and washed with hexane to give 5-hydroxy-1-methyl-3-trifuoromethylpyrazole (30.7 g) as a colorless solid, m.p. 170°–173° C.

B. Preparation of 5-Methyl-1-[1-methyl-3-(trifluoromethyl)-1H-pyrazol-5-yl]oy-2-nitrobenzene 5-Hydroxy-1-methyl-3-trifluoromethylpyrazole (8.30 g, 50 mmol) and powdered potassium carbonate (8.29 g, 60 mmol) were stirred together in dimethylsulfoxide (40 ml) for 30 minutes. 3-Fluoro-4-nitrotoluene (7.76 g, 50 mmol) was added and the mixture heated at 70° C. for 17 h, then cooled to room temperature. The mixture was partitioned between diethyl ether and water, the ethereal extract washed with water and brine, dried over magnesium sulfate, filtered and the filtrate evaporated. The residue was further purified by flash column chromatography over silica gel, and the desired fraction collected and triturated with hexane to give the desired product as a pale yellow solid (6.20 g), m.p. 88°–90° C.

C. Preparation of 2-Amino-5-methyl-1-[1-methyl-3-(trifluoromethyl)-1H-pyrazol-5-yl]oxyphenyl]oxybenzene 5% Palladium on charcoal (0.2 g) was added to a solution of the compound prepared in B above (2.00 g, 6.6 mmol) in ethanol (50 ml) and the mixture shaken in a Parr hydrogenator at 50 p.s.i. for 2 h. The catalyst was removed by filtration and the filtrate evaporated in vacuo. The residue was further purified by flash column chromatography over silica gel, and the desired amine obtained as a pale pink oil (1.73 g).

D. Preparation of N-[4Methyl-2-[1-methyl-3-(trifluoromethyl)-1H-pyrazol-5-yl]oxyphenyl]cyclopropane carboxamide Cyclopropylcarbamyl chloride (0.22 ml, 0.25 g, 2.4 mmol) was added to a mixture of triethylamine (0.50 ml, 0.36 g, 3.6 mmol) and the amine prepared in C above (0.66 g, 2.4 mmol) in dichloromethane (10 ml) and the mixture stirred at room temperature for 23 h. The mixture was partitioned between diethyl ether and water, the ethereal extract washed with water and brine, dried over magnesium sulfate, filtered and the filtrate evaporated. Trituration with hexane gave Compound 1 (0.56 g) as a colorless solid, m.p. 126°–128° C.

Example 2

Starting from the amine prepared in Example 1 C, Compounds 2–5 were prepared by similar processes using appropriate starting materials.

Example 3

Preparation of Isopropyl N-[4,5dichloro-2-[1-methyl-3-(trifluoromethyl)-1H-pyrazol-5-yl] oxybenzenecarbamate Compound 18

A. Preparation of 4,5-Dichloro-1-[1-methyl-3-(trifluoromethyl)-1H-pyrazol-5-yl]oxy2-nitrobenzene 5-Hydroxy-1-methyl-3-trifluoromethylpyrazole (7.0 g, 40 mmol) and powdered potassium carbonate (11.4 g, 80 mmol) were stirred together in dimethylsulfoxide (40 ml) for 30 minutes. 4,5-Dichloro-2-fluoronitrobenzene (7.9 g, 50 mmol) was added and the mixture stirred at room temperature for 18 h. The mixture was partitioned between diethyl ether and water, the ethereal extract washed with water and brine, dried over magnesium sulfate, filtered and the filtrate evaporated. The residue was further purified by flash column chromatography over silica gel, to give the desired product (5.9 g) as a light yellow solid, m.p. 99°–100° C.

B. Preparation of 2-Amino-4,5dichloro-2-[1-methyl-3-(trifluoromethyl)-1H-pyrazol-5-yl]oxybenzene Raney Nickel (ca. 0.5 g) was added to a solution of the compound prepared in A above (5.5 g, 16 mmol) in ethanol (100 ml) and the mixture shaken in a Parr hydrogenator at 50 p.s.i. for 2 h. The catalyst was removed by filtration and the filtrate evaporated in vacuo to give the desired product as a pale solid (4.7 g), m.p. 126°–128° C.

C. Preparation of Isopropyl N-[4,5dichloro-2-[1-methyl-3 (trifluoromethyl)-1H-pyrazol-5-yl]oybenzenecarbamate The amine prepared in B above (1.0 g, 3 mmol) was added to a chilled (ice-bath) mixture of isopropylchloroformate (1M solution in toluene, 7 ml, 7 mmol) and triethylamine (0.6 g, mmol) and the mixture stirred for 18 h. The mixture was partitioned between diethyl ether and water, the ethereal extract washed with water and brine, dried over magnesium sulfate, filtered and the filtrate evaporated. The residue was further purified by flash column chromatography over silica gel, to give the desired product (0.2 g) as a colorless solid, m.p. 125°–126° C.

Example 4

N-[4-Methoxy-2-[1-methyl-3(trifluoromethyl)-1H-pyrazol-5yl]oxyphenyl]cyclopropanecarboxamide Compound 20

A. Preparation of 5Fluoro-1-[2-methyl-3(trifluoromethyl)-1H-pyrazol-5-yl]oxy-2-nitrobenzene 5-Hydroxy-1-methyl-3-trifluoromethylpyrazole (8.3 g, 50 mmol) and powdered potassium carbonate (8.3 g, 60 mmol) were stirred together in dimethylsulfoxide (40 ml) for 30 minutes. 2,4-Difluoronitrobenzene (7.9 g, 50 mmol) was added and the mixture stirred at room temperature for 18 h. The mixture was partitioned between diethyl ether and water, the ethereal extract washed with water and brine, dried over magnesium sulfate, filtered and the filtrate evaporated. The residue was further purified by flash column chromatography over silica gel, to give the desired product (2.3 g) as a solid. m.p. 68°–70° C.

B. Preparation of 5-Methoxy-1-[1-methyl-3(trifluoromethyl)-1H-pyrazol-5-yl]oxy-2-nitrobenzene The compound prepared in A above (1.5 g, 5 mmol) was dissolved in methanol (20 ml) and sodium methoxide (25% solution in methanol, 1.1 ml, 5 mmol) added. The mixture was stirred at room temperature for 3 h, then partitioned between diethyl ether and water. The ethereal extract was washed with water and brine, dried over magnesium sulfate, filtered and the filtrate evaporated. The residue was triturated with hexane to give the desired product (0.8 g) as a yellow solid.

C. Preparation of 2-Amino-5-methoxy-1-[1-methyl-3(trifluoromethyl)-1H-pyrazol-5-yl]oxybenzene Raney Nickel (ca. 0.08 g) was added to a solution of the compound prepared in B above (0.8 g, 2.5 mmol) in methanol (50 ml) and the mixture shaken in a Parr hydrogenator at 50 p.s.i. for 1 h. The catalyst was removed by filtration and the filtrate evaporated in vacuo. The product was used without further purification in D below.

D. Preparation of N-[4-Methoxy-2-[1-methyl-3(trifluoromethyl)-1H-pyrazol-5-yl]oxyphenyl] cyclopropanecarboxamide Cyclopropylcarbamyl chloride (0.2 g, 1.4 mmol) was added to a mixture of triethylamine (0.3 g, 2.8 mmol) and the amine prepared in C above (0.4 g, 1.4 mmol) in dichloromethane (10 ml) and the mixture stirred at room temperature for 30 minutes. The mixture was partitioned between diethyl ether and water, the ethereal extract washed with water and brine, dried over magnesium sulfate, filtered and the filtrate evaporated. Trituration with hexane gave Compound 20 (0.4 g) as a colorless solid. m.p. 140°–142° C.

Example 5

N-[4-Methyl-2-[1-methyl-3-(trifluoromethyl)-1H-pyrazol-5yl]thiophenyl]-cyclopropane carboxamide Compound 142

A. Preparation of 5thio-1-methyl-3trifluoromethylpyrazole

A. 5-hydroxy-1-methyl-3-trifluoromethylpyrazole (30 g, 180 mmol) (Example 1, Part A) was dissolved in toluene (250 mL). Lawesson's reagent (36.5 g, 90 mmol) was added and the mixture was heated to reflux for 8 hours. An additional 10.0 g (20 mmol) of Lawesson's reagent was added and the mixture continued at reflux for 2 hours. The mixture was allowed to cool, stirring at room temperature for 18 hours. The solution was poured into saturated aqueous sodium carbonate solution and partitioned. The resulting aqueous phase was acidified to pH 2 with concentrated hydrochloric acid. The mixture was extracted with diethyl ether, dried over magnesium sulfate, filtered and the filtrate evaporated to give the desired product as a yellow oil (26 g).

B. Preparation of 5Methyl-1-[1-methyl-3(trifluoromethyl)-1H-pyrazol-5yl]thio-2-nitrobenzene B. The thiol prepared in step A above, (5 g, 17 mmol) was dissolved in 4-methyl-2-pentanone (50 mL). To this was added 3-fluoro4-nitrotoluene (2.6 g, 17 mmol) and the mixture was stirred for 5 min. Potassium carbonate (3.2 g, 22 mmol) was added and the mixture was heated to reflux for 2 hours. The heat was removed and the mixture was cooled to room temperature. The mixture was poured into water and this was neutralized with acetic acid. The resulting mixture was partitioned between diethyl ether and water, the ethereal extract was washed with water, dried over magnesium sulfate, filtered and the filtrate evaporated. Trituration with hexane gave the desired compound (2.0 g) as a yellow solid, m.p. 98°–100° C.

C. Preparation of 2-Amino-5methyl-1-[1-methyl-3(trifluoromethyl)-1H-pyrazol-5-yl]thiobenzene C. The nitrotoluene prepared above (1.8 g, 5.7 mmol) was added to methanol (50 mL). Palladium on carbon (0.1 g, 5%) was added and the mixture was hydrogenated at 50 p.s.i. for 3 hours. The catalyst was removed by filtration and the filtrate evaporated. The resulting residue was triturated with hexane to give the desired product as a yellow solid (0.8 g) m.p. 64°–68° C.

D. Preparation of N-[4-Methyl-2-[1-methyl-3-(trifluoromethyl)-1H-pyrazol-5-yl]thiophenyl]cyclopropane carboxamide D. Cyclopropanecarbonyl chloride (0.3 g, 3 mmol) and triethylamine (0.5g, 4.5 mmol) were added dropwise to a chilled (ice-bath) solution of the aniline prepared in Step C above (0.7 g, 2.4 mmol) in dichloromethane (20 mL). The reaction was stirred at room temperature for 24 hours, then partitioned between diethyl ether and water. The ethereal extract was dried over magnesium sulfate, filtered and the filtrate evaporated. Trituration with hexane gave Compound 142 (0.55 g) as a yellow solid, m.p. 162°–164° C.

Example 6

Preparation of Isopropyl N-[4,5dichloro-2-[1-methyl-3-(trifluoromethyl)-1H-pyrazol-5yl] thiobenzenecarbamate Compound 143

Triphosgene (0.6 g, 2 mmol) was added to a solution of the aniline prepared in Step C in Example 5 above (1.25 g, 4 mmol) in ethyl acetate (20 mL) and the mixture was heated at reflux for 1 hour. The mixture was cooled to room temperature and the solvent removed by rotary evaporation. The residue was dissolved in isopropanol (20mL) and stirred at room temperature for 1 hour, then the solvent was evaporated. Trituration with hexane gave Compound 2 (1.0 g) as a colorless solid, m.p. 118°–120° C.

TABLE I

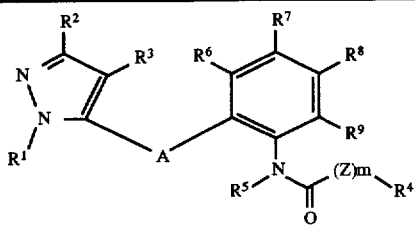

| Comp. No. | R$^1$ | R$^2$ | R$^3$ | R$^4$ | R$^5$ | R$^6$ | R$^7$ | R$^8$ | R$^9$ | A | m* | Z | m.p. (°C.) |
|---|---|---|---|---|---|---|---|---|---|---|---|---|---|
| 1 | CH$_3$ | CF$_3$ | H | cyclopropyl | H | H | CH$_3$ | H | H | O | 0 | — | 126–128 |
| 2 | CH$_3$ | CF$_3$ | H | tert-butyl | H | H | CH$_3$ | H | H | O | 0 | — | 73–75 |
| 3 | CH$_3$ | CF$_3$ | H | CF$_3$ | H | H | CH$_3$ | H | H | O | 0 | — | 95–97 |
| 4 | CH$_3$ | CF$_3$ | H | CH(CH$_3$)$_2$ | H | H | CH$_3$ | H | H | O | 0 | — | 130–132 |
| 5 | CH$_3$ | CF$_3$ | H | CH$_2$CH$_3$ | H | H | CH$_3$ | H | H | O | 0 | — | 96–98 |
| 6 | CH$_3$ | CF$_3$ | H | CH(CH$_3$)$_2$ | H | H | CH$_3$ | H | H | O | 1 | O | 68–70 |
| 7 | CH$_3$ | CF$_3$ | H | C$_2$H$_5$ | H | H | CH$_3$ | H | H | O | 1 | O |  |
| 8 | CH$_3$ | CF$_3$ | H | cyclopropyl | H | H | F | H | H | O | 0 | — | 125–127 |
| 9 | CH$_3$ | CF$_3$ | H | CH(CH$_3$)$_2$ | H | H | F | H | H | O | 1 | O | 125–127 |
| 10 | CH$_3$ | CF$_3$ | H | cyclopropyl | H | H | Cl | H | H | O | 0 | — | 130–132 |
| 11 | CH$_3$ | CF$_3$ | H | C$_2$H$_5$ | H | H | Cl | H | H | O | 1 | O | 93–97 |
| 12 | CH$_3$ | CF$_3$ | H | C$_2$H$_5$ | H | H | CH$_3$ | H | H | O | 1 | S | 90–92 |
| 13 | CH$_3$ | CF$_3$ | H | cyclopropyl | H | H | H | CH$_3$ | H | O | 0 | — | 138–140 |
| 14 | CH$_3$ | CF$_3$ | H | cyclopropyl | H | H | Cl | Cl | H | O | 0 | — | 158–160 |
| 15 | CH$_3$ | CF$_3$ | H | CH(CH$_3$)$_2$ | H | H | H | CH$_3$ | H | O | 1 | O | — |
| 16 | CH$_3$ | CF$_3$ | H | CH(CH$_3$)$_2$ | H | H | H | CH$_3$ | H | O | 0 | — | 125–126 |
| 17 | CH$_3$ | CF$_3$ | H | CH(CH$_3$)$_2$ | H | H | Cl | Cl | H | O | 1 | O | 92–94 |
| 18 | CH$_3$ | CF$_3$ | H | CH(CH$_3$)$_2$ | H | H | Cl | Cl | H | O | 0 | — | 144–145 |
| 19 | CH$_3$ | CF$_3$ | H | cyclopropyl | H | H | OCH$_3$ | H | H | O | 0 | — | 140–142 |
| 20 | CH$_3$ | CF$_3$ | H | CH$_3$ | H | H | CH$_3$ | H | H | O | 0 | — | 142–144 |
| 21 | CH$_3$ | CF$_3$ | H | 1-methylcyclopropyl | H | H | CH$_3$ | H | H | O | 0 | — | 100–103 |
| 22 | CH$_3$ | CF$_3$ | H | CH(Cl)$_2$ | H | H | CH$_3$ | H | H | O | 0 | — | 130–132 |
| 23 | CH$_3$ | CF$_3$ | H | CH=CH$_2$ | H | H | CH$_3$ | H | H | O | 0 | — | 147–149 |
| 24 | CH$_3$ | CF$_3$ | H | CH=C(CH$_3$)$_2$ | H | H | CH$_3$ | H | H | O | 0 | — | 116–118 |
| 25 | CH$_3$ | CF$_3$ | H | CH$_2$C(CH$_3$)=CH$_2$ | H | H | CH$_3$ | H | H | O | 0 | — | 83–85 |
| 26 | CH$_3$ | isopropyl | H | cyclopropyl | H | H | CH$_3$ | H | H | O | 0 | — | 135–137 |
| 27 | CH$_3$ | CF$_3$ | H | CH(CH$_3$)CH$_2$CH$_3$ | H | H | CH$_3$ | H | H | O | 1 | S | 93–95 |
| 28 | CH$_3$ | CF$_3$ | H | CH(CH$_3$)$_2$ | H | H | CH$_3$ | H | H | O | 1 | S | 104–105 |
| 29 | CH$_3$ | CF$_3$ | H | CH$_2$C(CH$_3$)$_3$ | H | H | CH$_3$ | H | H | O | 0 | — | 142–143 |
| 30 | CH$_3$ | CF$_3$ | H | CH$_2$CH(CH$_3$)$_2$ | H | H | CH$_3$ | H | H | O | 0 | — | 128–130 |
| 31 | CH$_3$ | C$_2$F$_5$ | H | C$_2$H$_5$ | H | H | CH$_3$ | H | H | O | 1 | O |  |
| 32 | CH$_3$ | C$_2$F$_5$ | H | cyclopropyl | H | H | CH$_3$ | H | H | O | 0 | — | 161–163 |
| 33 | CH$_3$ | CF$_3$ | H | CH(CH$_3$)$_2$ | H | H | OCH$_3$ | H | H | O | 0 | — | 128–130 |
| 34 | CH$_3$ | CF$_3$ | H | CH(CH$_3$)$_2$ | H | H | OCH$_3$ | H | H | O | 1 | O | 77–79 |
| 35 | CH$_3$ | cyclopropyl | H | cyclopropyl | H | H | CH$_3$ | H | H | O | 0 | — | 133–135 |
| 36 | CH$_3$ | isopropyl | H | C$_2$H$_5$ | H | H | CH$_3$ | H | H | O | 1 | O | 71–74 |
| 37 | CH$_3$ | cyclopropyl | H | CH(CH$_3$)$_2$ | H | H | CH$_3$ | H | H | O | 0 | — | 129–131 |
| 38 | CH$_3$ | cyclopropyl | H | CH(CH$_3$)$_2$ | H | H | CH$_3$ | H | H | O | 1 | O | — |
| 39 | CH$_3$ | CF$_3$ | H | cyclopropyl | CH$_3$ | H | CH$_3$ | H | H | O | 0 | — | 75–77 |
| 40 | CH$_3$ | CF$_3$ | H | cyclopropyl | CH$_3$OCH$_2$ | H | CH$_3$ | H | H | O | 0 | — | 103–105 |
| 41 | CH$_3$ | CF$_3$ | Br | cyclopropyl | H | H | CH$_3$ | H | H | O | 0 | — | 163–165 |
| 42 | CH$_3$ | CF$_3$ | H | C$_2$H$_5$ | H | H | OCH$_3$ | H | H | O | 1 | S | 80–83 |
| 43 | CH$_3$ | CF$_3$ | H | C$_2$H$_5$ | H | H | OCH$_3$ | H | H | O | 1 | O |  |
| 44 | CH$_3$ | CF$_3$ | H | CH$_2$Cl | H | H | CH$_3$ | H | H | O | 0 | — | 105–107 |
| 45 | CH$_3$ | CF$_3$ | H | CH$_3$ | H | H | CH$_3$ | H | H | O | 1 | O |  |
| 46 | CH$_3$ | CF$_3$ | H | CH$_2$-cyclopentane | H | H | CH$_3$ | H | H | O | 0 | — | 135–137 |
| 47 | CH$_3$ | CF$_3$ | H | CH$_2$CH(CH$_3$)$_2$ | H | H | CH$_3$ | H | H | O | 1 | O | 108–110 |
| 48 | CH$_3$ | CF$_3$ | H | CH$_2$C(CH$_3$)$_3$ | H | H | CH$_3$ | H | H | O | 1 | O | 103–105 |
| 49 | CH$_3$ | CF$_3$ | H | cyclopentyl | H | H | CH$_3$ | H | H | O | 1 | O | 83–85 |
| 50 | CH$_3$ | CF$_3$ | H | CH=NOH | H | H | CH$_3$ | H | H | O | 0 | — | 161–166 |
| 51 | CH$_3$ | CF$_3$ | H | CH$_2$-c-propyl | H | H | CH$_3$ | H | H | O | 1 | O | 82–84 |
| 52 | CH$_3$ | CF$_3$ | H | CH(CH$_3$)CH$_2$CH$_3$ | H | H | CH$_3$ | H | H | O | 1 | O | 38–40 |
| 53 | CH$_3$ | CF$_3$ | H | CH$_2$CF$_3$ | H | H | CH$_3$ | H | H | O | 1 | O | 84–85 |
| 54 | CH$_3$ | CF$_3$ | H | CH$_2$CH=CH$_2$ | H | H | CH$_3$ | H | H | O | 1 | O | 70–74 |
| 55 | CH$_3$ | CF$_3$ | H | CH$_2$C(CH$_3$)=CH$_2$ | H | H | CH$_3$ | H | H | O | 1 | O | 87–90 |
| 56 | CH$_3$ | CF$_3$ | H | CH$_2$C.CH | H | H | CH$_3$ | H | H | O | 1 | O | 98–100 |
| 57 | CH$_3$ | CF$_3$ | H | (CH$_2$)$_3$Br | H | H | CH$_3$ | H | H | O | 0 | — | 117–118 |
| 58 | CH$_3$ | CF$_3$ | H | CH$_2$CH$_2$CH$_3$ | H | H | CH$_3$ | H | H | O | 1 | O | 94–95 |
| 59 | CH$_3$ | CF$_3$ | H | CH$_2$CH(CH$_3$)$_2$ | H | H | CH$_3$ | H | H | O | 1 | S | 100–102 |
| 60 | CH$_3$ | CF$_3$ | H | cyclopropyl | H | H | H | H | H | O | 0 | — | 123–126 |
| 61 | CH$_3$ | CF$_3$ | H | CH(CH$_3$)$_2$ | H | H | H | H | H | O | 1 | O | 74–77 |
| 62 | CH$_3$ | CF$_3$ | Br | cyclopropyl | H | H | H | H | H | O | 0 | — | 139–141 |
| 63 | CH$_3$ | CF$_3$ | Br | CH(CH$_3$)$_2$ | H | H | H | H | H | O | 1 | O | — |
| 64 | CH$_3$ | CF$_3$ | H | cyclopropyl | H | H | SCH$_3$ | H | H | O | 0 | — | 117–120 |

TABLE I-continued

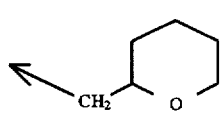

| Comp. No. | R¹ | R² | R³ | R⁴ | R⁵ | R⁶ | R⁷ | R⁸ | R⁹ | A | m* | Z | m.p. (°C.) |
|---|---|---|---|---|---|---|---|---|---|---|---|---|---|
| 65 | CH₃ | CF₃ | H | CH₂CH(CH₃)₂ | H | H | CH₃ | H | H | O | 1 | S | — |
| 66 | CH₃ | CF₃ | H | C₂H₅ | H | H | CH₃ | H | H | O | 1 | S | — |
| 67 | CH₃ | CF₃ | H | cyclopropyl | H | H | C₂H₅ | H | H | O | 0 | — | 173–175 |
| 68 | CH₃ | CF₃ | H | CH(CH₃)₂ | H | H | OCH₂CH₃ | H | H | O | 1 | O | 83–85 |
| 69 | CH₃ | CF₃ | Br | CH(CH₃)₂ | H | H | Br | H | H | O | 1 | O | 131–133 |
| 70 | CH₃ | CF₃ | H | CH(CH₃)₂ | H | H | CH₃ | H | H | O | 1 | S | 95–98 |
| 71 | CH₃ | CF₃ | H | CH₂-cyclopropane | H | H | CH₃ | H | H | O | 0 | — | 95–97 |
| 72 | CH₃ | CF₃ | H | CH(CH₃)CO₂-n-C₄H₉ | H | H | CH₃ | H | H | O | 1 | O | — |
| 73 | CH₃ | CF₃ | H | CH(CH₃)CH₂CO₂C₂H₅ | H | H | CH₃ | H | H | O | 1 | O | — |
| 74 | CH₃ | CF₃ | Br | CH(CH₃)₂ | H | H | I | H | H | O | 1 | O | 148–150 |
| 75 | CH₃ | CF₃ | H | 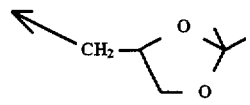 | H | H | CH₃ | H | H | O | 1 | O | 80–83 |
| 76 | CH₃ | CF₃ | H | 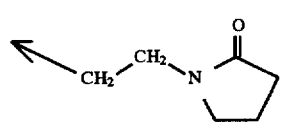 | H | H | CH₃ | H | H | O | 1 | O | — |
| 77 | CH₃ | CF₃ | H | CH₂CH₂OCH₃ | H | H | CH₃ | H | H | O | 1 | O | — |
| 78 | CH₃ | CF₃ | H | CH₂C(CH₃)₂COOCH₃ | H | H | CH₃ | H | H | O | 1 | O | 84–85 |
| 79 | CH₃ | CF₃ | H | CH₂CH₂N(CH₃)₂ | H | H | CH₃ | H | H | O | 1 | O | — |
| 80 | CH₃ | CF₃ | H | CH₂CH₂Br | H | H | CH₃ | H | H | O | 1 | O | 78–80 |
| 81 | CH₃ | CF₃ | H | CH(CH₃)CH₂Cl | H | H | CH₃ | H | H | O | 1 | O | — |
| 82 | CH₃ | CF₃ | H | CH₂CCl₃ | H | H | CH₃ | H | H | O | 1 | O | 108–110 |
| 83 | CH₃ | CF₃ | H | phenyl | H | H | CH₃ | H | H | O | 0 | — | 140–142 |
| 84 | CH₃ | CF₃ | H | 4-F-phenyl | H | H | CH₃ | H | H | O | 0 | — | 152–154 |
| 85 | CH₃ | CF₃ | H | 2-methylcyclopropyl | H | H | CH₃ | H | H | O | 0 | — | 132–134 |
| 86 | CH₃ | CF₃ | H | 4-CN-phenyl | H | H | CH₃ | H | H | O | 0 | — | 158–160 |
| 87 | CH₃ | CF₃ | H | OCH(C₂H₅)C.CH | H | H | CH₃ | H | H | O | 1 | O | 70–72 |
| 88 | CH₃ | CF₃ | H | CH₂CH₂F | H | H | CH₃ | H | H | O | 1 | O | 60–62 |
| 89 | CH₃ | CF₃ | H | CH(CH₃)C.CH | H | H | CH₃ | H | H | O | 1 | O | 112–113 |
| 90 | CH₃ | CF₃ | H | CH(CH₃)CH=CHCH₃ | H | H | CH₃ | H | H | O | 1 | O | 64–66 |
| 91 | CH₃ | CF₃ | H | CH(CH₃)CH=CH₂ | H | H | CH₃ | H | H | O | 1 | O | 64–66 |
| 92 | CH₃ | CF₃ | H | (CH₂CH₂-N-pyrrolidinone) | H | H | CH₃ | H | H | O | 1 | O | 80–83 |
| 93 | CH₃ | CF₃ | H | CH(CH₃)CF₃ | H | H | CH₃ | H | H | O | 1 | O | 92–94 |
| 94 | CH₃ | CF₃ | H | CH=NOCH₃ | H | H | CH₃ | H | H | O | 0 | — | |
| 95 | CH₃ | CF₃ | H | COCH₃ | H | H | CH₃ | H | H | O | 0 | — | |
| 96 | CH₃ | CF₃ | H | C(CH₃)₃ | H | H | CH₃ | H | H | O | 1 | O | 95–97 |
| 97 | CH₃ | CF₃ | H | CH₂OCH₃ | H | H | CH₃ | H | H | O | 0 | — | 92–94 |
| 98 | CH₃ | CF₃ | H | C(Cl)₃ | H | H | CH₃ | H | H | O | 0 | — | 105–109 |
| 99 | CH₃ | CF₃ | H | 3-pyridyl | H | H | CH₃ | H | H | O | 0 | — | 99–100 |
| 100 | CH₃ | C₂F₅ | H | CH₂CH(CH₃)₂ | H | H | CH₃ | H | H | O | 0 | — | 148–150 |
| 101 | CH₃ | C₂F₅ | H | CH=C(CH₃)₂ | H | H | CH₃ | H | H | O | 0 | — | 113–115 |
| 102 | CH₃ | C₂F₅ | H | CH₂C(CH₃)₃ | H | H | CH₃ | H | H | O | 0 | — | 128–130 |
| 103 | CH₃ | C₂F₅ | H | CH(CH₃)₂ | H | H | CH₃ | H | H | O | 1 | O | 85–87 |
| 104 | CH₃ | CF₃ | H | CH₃ | H | H | H | H | H | O | 0 | — | 105–110 |
| 105 | CH₃ | CF₃ | H | CH(CH₃)₂ | H | H | Cl | H | H | O | 0 | — | 82–84 |
| 106 | CH₃ | CF₃ | H | 3-tetrahydrofuryl | H | H | CH₃ | H | H | O | 1 | O | 86–88 |
| 107 | CH₃ | CF₃ | H | 3-methylcyclopentyl | H | H | CH₃ | H | H | O | 1 | O | 88–90 |
| 108 | CH₃ | CF₃ | H | C(CH₃)=CH₂ | H | H | CH₃ | H | H | O | 1 | O | 67–69 |
| 109 | CH₃ | CF₃ | H | CH(CH₂F)₂ | H | H | CH₃ | H | H | O | 1 | O | 108–110 |
| 110 | CH₃ | CF₃ | H | CH₂CH₂Cl | H | H | CH₃ | H | H | O | 0 | — | 98–100 |
| 111 | CH₃ | CF₃ | H | 2-furyl | H | H | CH₃ | H | H | O | 0 | — | 99–100 |

TABLE I-continued

| Comp. No. | R¹ | R² | R³ | R⁴ | R⁵ | R⁶ | R⁷ | R⁸ | R⁹ | A | m* | Z | m.p. (°C.) |
|---|---|---|---|---|---|---|---|---|---|---|---|---|---|
| 112 | $CH_3$ | $CF_3$ | H | 3-chloro-3-methylcyclopentan-1-on-1-yl | H | H | $CH_3$ | H | H | O | 0 | — | gum |
| 113 | $CH_3$ | $CF_3$ | H | $C(CH_3)_2CH_2Cl$ | H | H | $CH_3$ | H | H | O | 0 | — | 93–95 |
| 114 | $CH_3$ | $CF_3$ | H | $CH=CH=CHCH_3$ | H | H | $CH_3$ | H | H | O | 0 | — | 155–157 |
| 115 | $CH_3$ | $CF_3$ | H | $CH_2CO_2CH_2CH_3$ | H | H | $CH_3$ | H | H | O | 0 | — | 110–112 |
| 116 | $CH_3$ | $CF_3$ | H | $CH_2CH_2CO_2CH_3$ | H | H | $CH_3$ | H | H | O | 0 | — | 102–103 |
| 117 | $CH_3$ | $CF_3$ | H | $CO_2CH_3$ | H | H | $CH_3$ | H | H | O | 0 | — | 142–144 |
| 118 | $CH_3$ | $CF_3$ | H | cyclopropyl | H | H | Br | H | H | O | 0 | — | 130–132 |
| 119 | $CH_3$ | $CF_3$ | Cl | $CH(CH_3)_2$ | H | H | $CH_3$ | H | H | O | 1 | O | 91–93 |
| 120 | $CH_3$ | $CF_3$ | H | $C(CH_3)=CH_2$ | H | H | $CH_3$ | H | H | O | 0 | — | 88–90 |
| 121 | $CH_3$ | $CF_3$ | H | 5-nitro-2-furyl | H | H | $CH_3$ | H | H | O | 0 | — | 155–158 |
| 122 | $CH_3$ | $CF_3$ | H | cyclobutyl | H | H | $CH_3$ | H | H | O | 0 | — | 122–123 |
| 123 | $CH_3$ | $CF_3$ | H | $(CH_2)_3CO_2CH_2CH_3$ | H | H | $CH_3$ | H | H | O | 0 | — | 93–95 |
| 124 | $CH_3$ | $CF_3$ | H | $CH_2$-2-thiophenyl | H | H | $CH_3$ | H | H | O | 0 | — | 104–105 |
| 125 | $CH_3$ | $CF_3$ | H | $CHClCH_3$ | H | H | $CH_3$ | H | H | O | 0 | — | 127–129 |
| 126 | $CH_3$ | $CF_3$ | H | $CF_2CF_3$ | H | H | $CH_3$ | H | H | O | 0 | — | 58–60 |
| 127 | $CH_3$ | $CF_3$ | H | $C(Br)=CH_2$ | H | H | $CH_3$ | H | H | O | 0 | — | 83–84 |
| 128 | $CH_3$ | $CF_3$ | H | $CH(Br)CH_3$ | H | H | $CH_3$ | H | H | O | 0 | — | 134–135 |
| 129 | $CH_3$ | $CF_3$ | H | 2,2-dichlorocyclopropyl | H | H | $CH_3$ | H | H | O | 0 | — | 135–137 |
| 130 | $CH_3$ | $CF_3$ | H | $CH=C(CH_3)CF_3$ | H | H | $CH_3$ | H | H | O | 0 | — | 163–165 |
| 131 | $CH_3$ | $CF_3$ | H | $CH=CHCl$ | H | H | $CH_3$ | H | H | O | 0 | — | 154–155 |
| 132 | $CH_3$ | $CF_3$ | H | 2,2-dichlorocyclopropyl | H | H | $CH_3$ | H | H | O | 0 | — | 144–145 |
| 133 | $CH_3$ | $CF_3$ | H | $C(Cl)=CCl_2$ | H | H | $CH_3$ | H | H | O | 0 | — | 97–100 |
| 134 | $CH_3$ | $CF_3$ | H | 3-methyl-2-thiophenyl | H | H | $CH_3$ | H | H | O | 0 | — | 123–125 |
| 135 | $CH_3$ | $CF_3$ | H | $CH=C(CF_3)_2$ | H | H | $CH_3$ | H | H | O | 0 | — | 158–160 |
| 136 | $CH_3$ | $CF_3$ | H | $CH_2SCH_3$ | H | H | $CH_3$ | H | H | O | 0 | — | 119–121 |
| 137 | $CH_3$ | $CF_3$ | H | 2-cyanocyclopropyl | H | H | $CH_3$ | H | H | O | 0 | — | 110–112 |
| 138 | $CH_3$ | $CF_3$ | H | cyclopentyl | H | H | $CH_3$ | H | H | O | 0 | — | 143–144 |
| 139 | $CH_3$ | $CF_3$ | H | cyclopropyl | H | H | CN | H | H | O | 0 | — | 154–158 |
| 140 | $CH_3$ | $CF_3$ | H | $CH(CH_3)_2$ | H | H | CN | H | H | O | 1 | O | 101–103 |
| 141 | $CH_3$ | $CF_3$ | H | $CH_2C(CH_3)_3$ | H | H | CN | H | H | O | 0 | — | 101–104 |
| 142 | $CH_3$ | $CF_3$ | H | cyclopropyl | H | H | $CH_3$ | H | H | S | 0 | — | 162–164 |
| 143 | $CH_3$ | $CF_3$ | H | $=CH(CH_3)_2$ | H | H | $CH_3$ | H | H | S | 1 | O | 118–120 |
| 144 | $CH_3$ | $CF_3$ | H | $-CH=C(CH_3)_2$ | H | H | $CH_3$ | H | H | S | 0 | — | 124–125 |
| 145 | $CH_3$ | $CF_3$ | H | $=CH(CH_3)_2$ | H | H | $CH_3$ | H | H | S | 1 | N | 195 |
| 146 | $CH_3$ | $CF_3$ | H | 2-methylcyclopropyl | H | H | $CH_3$ | H | H | S | 0 | — | 161–162 |
| 147 | $CH_3$ | $CF_3$ | H | $C(Cl)=CH_2$ | H | H | $CH_3$ | H | H | O | 0 | — | 68–70 |
| 148 | $CH_3$ | $CF_3$ | H | $CH(CH_3)_2$ | H | H | $CH_3$ | H | H | SO | 1 | O | 110–112 |
| 149 | $CH_3$ | $CF_3$ | H | $CH(CH_3)_2$ | H | H | $CH_3$ | H | H | $SO_2$ | 1 | O | 148–149 |
| 150 | $C_2H_5$ | $CF_3$ | H | cyclopropyl | H | H | $CH_3$ | H | H | O | 0 | — | 138–140 |
| 151 | $C_2H_5$ | $CF_3$ | H | $CH(CH_3)_2$ | H | H | $CH_3$ | H | H | O | 1 | O | 100–102 |
| 152 | $C_2H_5$ | $CF_3$ | H | $CH(CH_3)_2$ | H | H | $CH_3$ | H | H | O | 0 | — | 140–142 |
| 153 | $CH_3$ | $CF_3$ | H | $CH=C(CH_3)_2$ | H | H | $CH_3$ | H | H | S | 0 | — | 103–104 |
| 154 | $C_2H_5$ | $CF_3$ | H | 2-methylcyclopropyl | H | H | $CH_3$ | H | H | O | 0 | — | 148–150 |

*) When m is 0, Z is a carbon-carbon single bond linking the carbonyl carbon to R⁴.

HERBICIDAL SCREENING TESTS

The compounds listed in the foregoing table were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

PRE-EMERGENCE HERBICIDAL SCREENING TEST

On the day preceding treatment, seeds of several different weed species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

The grass weeds planted (Table II) were broadleaf signalgrass (*Brachiaria platyphylla*) "BRAPP"; large crabgrass (*Digitaria sanguinalis*) "DIGSA"; barnyardgrass (*Echinochloa crusgalli*) "ECHCG"; rigid ryegrass (*Lolium rigidum*) "LOLRI"; fall panicum (*Panicum dichotomiflorum*) "PANDI"; giant foxtail (*Setari faberi*) "SETFA"; green foxtail (*Setaria viridis*) "SETVI"; blackgrass (*Alopecurus myosuroides*) "ALOMY"; wild oat (*Avena fatua*) "AVEFA" and Johnsongrass (*Sorghum halepense*) "SORHA".

The broadleaf weeds planted (Table III) were velvetleaf (*Abutilon theophrasti*) "ABUTH"; redroot pigweed (*Amaranthus retroflexus*) "AMARE"; common lambsquarters (*Chenopodium album*) "CHEAL"; ivyleaf morningglory (*Ipomoea hederacea*) "IPOHE"; common purslane (*Portulaca oleracea*) "POROL"; common cockleburr (*Xanthium strumarium*) "XANST"; and catchweed bedstraw (*Galium aparine*) "GALAP". Additionally, yellow nutsedge (*Cyperus esculentus*) "CYPES" nutlets were also sown.

Solutions of the test compounds were prepared by weighing out an appropriate amount of the test compound to provide an application rate of 0.25 kilograms per hectare (kg/ha), then dissolving the compound in a 50:50 mixture of deionized water and acetone containing 0.5% v/v Tween 20® (polyoxyethylene sorbitan monolaurate emulsifier) as a surfactant. Additional solvents, not exceeding 15% of spray volume, were used if needed to dissolve the compound.

The soil surface was sprayed inside an enclosed linear spray table with the nozzle set above the soil line. The spray table was calibrated to deliver 400 L/ha with the application rate being 0.25 kg/ha. After treatment, the flats were placed into a greenhouse and watered as needed. The greenhouse environmental systems provided the plants with natural and artificial lighting to attain 14 hours of light per day. Day and night temperatures were maintained at 29° and 21° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The results of the pre-emergence screening tests are shown in Tables II and III below. The control ratings range from 0 to 100 percent, where 0 represents no effect with growth equal to the untreated control and where 100 represents complete kill. The symbol "—" indicates that no test was performed at the 0.25 kg/ha level of application.

TABLE II

PRE-EMERGENCE SCREENING

| COMP. NO. | BRAPP | DIGSA | ECHCG | LOLRI | PANDI | SETFA | SETVI | ALOMY | AVEFA | SORHA |
|---|---|---|---|---|---|---|---|---|---|---|
| 1 | 100 | 100 | 100 | 100 | 100 | 100 | 100 | 100 | 100 | 100 |
| 2 | 35 | 50 | 15 | 20 | 40 | 40 | 50 | 20 | 5 | 25 |
| 3 | 0 | 0 | 0 | 0 | 0 | 0 | 15 | 0 | 0 | 0 |
| 4 | 100 | 100 | 100 | 85 | 100 | 100 | 100 | 100 | 100 | 100 |
| 5 | 100 | 100 | 100 | 75 | 100 | 100 | 100 | 95 | 90 | 90 |
| 6 | 100 | 100 | 100 | 100 | 100 | 100 | 100 | 100 | 100 | 100 |
| 7 | 100 | 100 | 98 | 60 | 100 | 100 | 100 | 90 | 75 | 95 |
| 8 | 50 | 100 | 40 | 20 | 60 | 100 | 90 | 60 | 15 | 40 |
| 9 | 35 | 65 | 15 | 15 | 50 | 40 | 98 | 30 | 5 | 15 |
| 10 | 100 | 100 | 100 | 98 | 100 | 100 | 100 | 95 | 90 | 100 |
| 11 | 60 | 100 | 25 | 35 | 50 | 70 | 100 | 65 | 10 | 35 |
| 12 | 90 | 100 | 100 | 65 | 100 | 100 | 100 | 98 | 75 | 100 |
| 13 | 0 | 0 | 0 | 0 | 0 | 5 | 5 | 0 | 0 | 0 |
| 14 | 60 | 90 | 30 | 35 | 60 | 65 | 70 | 50 | 50 | 40 |
| 15 | 0 | 0 | 5 | 5 | 0 | 0 | 5 | 0 | 0 | 0 |
| 16 | 0 | 0 | 0 | 0 | 0 | 0 | 5 | 0 | 0 | 0 |
| 17 | 10 | 20 | 25 | 0 | 15 | 15 | 20 | 25 | 0 | 10 |
| 18 | 15 | 25 | 15 | 0 | 25 | 25 | 35 | 35 | 10 | 25 |
| 19 | 100 | 100 | 100 | 90 | 100 | 100 | 100 | 98 | 85 | 100 |
| 20 | 65 | 100 | 50 | 20 | 100 | 90 | 90 | 50 | 50 | 50 |
| 21 | 100 | 100 | 70 | 25 | 98 | 100 | 100 | 90 | 70 | 70 |
| 22 | 0 | 0 | 0 | 0 | 0 | 5 | 35 | 0 | 0 | 0 |
| 23 | 50 | 80 | 60 | 40 | 70 | 60 | 80 | 40 | 25 | 60 |
| 24 | 100 | 100 | 100 | 50 | 100 | 100 | 100 | 98 | 65 | 100 |
| 25 | 100 | 100 | 100 | 85 | 100 | 100 | 100 | 98 | 90 | 100 |
| 26 | 80 | 100 | 90 | 20 | 100 | 100 | 100 | 80 | 50 | 100 |
| 27 | 90 | 100 | 5 | 10 | 70 | 80 | 90 | 40 | 10 | 50 |
| 28 | 100 | 100 | 100 | 40 | 100 | 100 | 100 | 100 | 40 | 100 |
| 29 | 100 | 100 | 100 | 80 | 100 | 100 | 100 | 100 | 95 | 100 |
| 30 | 100 | 100 | 100 | 100 | 100 | 100 | 100 | 100 | 100 | 100 |
| 31 | 90 | 100 | 60 | 30 | 95 | 100 | — | 70 | 5 | 100 |
| 32 | 100 | 100 | 100 | 100 | 100 | 100 | 100 | 100 | 80 | 100 |
| 33 | 100 | 100 | 90 | 20 | 100 | 100 | 80 | 80 | 80 | 90 |
| 34 | 100 | 100 | 90 | 70 | 100 | 100 | 100 | 100 | 50 | 90 |

TABLE II-continued

PRE-EMERGENCE SCREENING

| COMP. NO. | BRAPP | DIGSA | ECHCG | LOLRI | PANDI | SETFA | SETVI | ALOMY | AVEFA | SORHA |
|---|---|---|---|---|---|---|---|---|---|---|
| 35 | 60 | 90 | 10 | 0 | 70 | 0 | 100 | 20 | 0 | 20 |
| 36 | 0 | 0 | 0 | 0 | 0 | 0 | 0 | 0 | 0 | 0 |
| 37 | 0 | 40 | 0 | 0 | 0 | 0 | 90 | 0 | 0 | — |
| 39 | 0 | — | 0 | 0 | 0 | 0 | 0 | 0 | 0 | — |
| 40 | 0 | — | 0 | 0 | 0 | 0 | 0 | 0 | 0 | — |
| 41 | 0 | — | 0 | 0 | 5 | 10 | 5 | 0 | 0 | 0 |
| 42 | 85 | — | 70 | 30 | 95 | 100 | 100 | 85 | 25 | 90 |
| 43 | 40 | — | 20 | 0 | 35 | 100 | 100 | 50 | 5 | 15 |
| 44 | 0 | 0 | 0 | 0 | 0 | 0 | 0 | 0 | 0 | 0 |
| 45 | 90 | 100 | 50 | 20 | 90 | 100 | 100 | 90 | 60 | 70 |
| 46 | 80 | 100 | 70 | 50 | 100 | 100 | 100 | 85 | 65 | 70 |
| 47 | 35 | 85 | 5 | 0 | 15 | 60 | 90 | 20 | 10 | 15 |
| 48 | 60 | 50 | 5 | 0 | 30 | 30 | 35 | 0 | 0 | 10 |
| 49 | 60 | 100 | 25 | 15 | 50 | 90 | 100 | 35 | 10 | 50 |
| 50 | 0 | 0 | 0 | 0 | 0 | 0 | 0 | 0 | 0 | 0 |
| 51 | 10 | 50 | 0 | 0 | 50 | 60 | 100 | 30 | 0 | 0 |
| 52 | 70 | 100 | 40 | 30 | 90 | 100 | 100 | 60 | 10 | 10 |
| 53 | 80 | 100 | 30 | 30 | 100 | 100 | 100 | 40 | 5 | 80 |
| 54 | 40 | 100 | 10 | 0 | 90 | 90 | 100 | 30 | 0 | 0 |
| 55 | 30 | 100 | 20 | 20 | 50 | 80 | 100 | 40 | 0 | 20 |
| 56 | 80 | 100 | 30 | 20 | 100 | 100 | 100 | 70 | 5 | 40 |
| 57 | 0 | 0 | 0 | 0 | 0 | 0 | 30 | 0 | 0 | 0 |
| 58 | 90 | 100 | 10 | 0 | 90 | 90 | 100 | 40 | 20 | 0 |
| 59 | 90 | 100 | 35 | 60 | 95 | 100 | 100 | 55 | 25 | 25 |
| 60 | 0 | 20 | 0 | 0 | 0 | 0 | 50 | 0 | 0 | 0 |
| 64 | 25 | 90 | 0 | 0 | 40 | 10 | 10 | 0 | 0 | 20 |
| 65 | 5 | 10 | 0 | 0 | — | 20 | 90 | 30 | 0 | 0 |
| 66 | 70 | 100 | 10 | 0 | 90 | 90 | 100 | 70 | 10 | 60 |
| 67 | 20 | 30 | 0 | 0 | 0 | 0 | 70 | 0 | 0 | 0 |
| 68 | 0 | 0 | 0 | 0 | 0 | 0 | 0 | 0 | 0 | 0 |
| 70 | 95 | 100 | 100 | 70 | — | 100 | 100 | 90 | 40 | 20 |
| 71 | 0 | 20 | 0 | 5 | 30 | 10 | 20 | 10 | 20 | 0 |
| 72 | 0 | 0 | 0 | 0 | 0 | 0 | 0 | 0 | 0 | 0 |
| 73 | 0 | 0 | 0 | 0 | 0 | 0 | 0 | 0 | 0 | 0 |
| 75 | 0 | 0 | 0 | 0 | 0 | 0 | 0 | 0 | 0 | 0 |
| 76 | 5 | 0 | 0 | 0 | 0 | 0 | 0 | 0 | 0 | 0 |
| 78 | 30 | 0 | 0 | 0 | 0 | 0 | 0 | 0 | 0 | 0 |
| 79 | — | 0 | 0 | 0 | 0 | 0 | 0 | 0 | 0 | 0 |
| 80 | 0 | 30 | 0 | 0 | 0 | 0 | 0 | 0 | 0 | 0 |
| 81 | 100 | 100 | 60 | 30 | 70 | 100 | 100 | 70 | 40 | 70 |
| 82 | 100 | 100 | 30 | 50 | 100 | 100 | 100 | 95 | 20 | 60 |
| 83 | 30 | 20 | 0 | 0 | 40 | 0 | 100 | 0 | 0 | 0 |
| 84 | 100 | 98 | 60 | 40 | 100 | 98 | 100 | 60 | 60 | 80 |
| 85 | 100 | 100 | 100 | 100 | 100 | 100 | 100 | 100 | 100 | 100 |
| 86 | 30 | 100 | 5 | 0 | 40 | 40 | 80 | 0 | 0 | 0 |
| 87 | 20 | 100 | 20 | 40 | 30 | 30 | 100 | 80 | 40 | 40 |
| 88 | 50 | 100 | 30 | 0 | 50 | 70 | 100 | 70 | 30 | 20 |
| 89 | 100 | 100 | 80 | 80 | 100 | 100 | 100 | 90 | 80 | 90 |
| 90 | 0 | 0 | 0 | 0 | 0 | 0 | 30 | 30 | 0 | 0 |
| 91 | 80 | 100 | 80 | 80 | 90 | 90 | 100 | 90 | 40 | 40 |
| 92 | 45 | 0 | 0 | 0 | 0 | 0 | 0 | 0 | 0 | 0 |
| 93 | 100 | 100 | 80 | 65 | 100 | 100 | 100 | 75 | 70 | 70 |
| 94 | 10 | 98 | 5 | 10 | 15 | 70 | 100 | 20 | 0 | 15 |
| 95 | 0 | 0 | 0 | 0 | 0 | 0 | 0 | 0 | 0 | 0 |
| 96 | 100 | 100 | 65 | 50 | 100 | 100 | 100 | 90 | 60 | 50 |
| 97 | 0 | 0 | 0 | 0 | 0 | 0 | 0 | 0 | 0 | 0 |
| 98 | 25 | 100 | 15 | 10 | 40 | 50 | 100 | 60 | 25 | 5 |
| 99 | 5 | 100 | 0 | 0 | 15 | 15 | 40 | 20 | 5 | 5 |
| 100 | 100 | 100 | 100 | 70 | 100 | 100 | 100 | 100 | 80 | 100 |
| 101 | 100 | 100 | 100 | 80 | 100 | 100 | 100 | 90 | 50 | 70 |
| 102 | 100 | 100 | 85 | 60 | 100 | 100 | 100 | 75 | 25 | 80 |
| 103 | 100 | 100 | 100 | 100 | 100 | 100 | 100 | 100 | 70 | 100 |
| 105 | 85 | 100 | 80 | 80 | 98 | 100 | 100 | 90 | 70 | 80 |
| 106 | 30 | 100 | 30 | 10 | — | 90 | 100 | 50 | 10 | 20 |
| 107 | 40 | 100 | 10 | 30 | — | 100 | 100 | 70 | 10 | 10 |
| 108 | 100 | 100 | 100 | 100 | — | 100 | 100 | 90 | 100 | 90 |
| 110 | 40 | 100 | 40 | 30 | — | 100 | 100 | 70 | 70 | 30 |
| 111 | 0 | 20 | 0 | 0 | — | 0 | 70 | 5 | 0 | 0 |
| 112 | 0 | 0 | 0 | 0 | — | 0 | 0 | 0 | 0 | 0 |
| 113 | 0 | 0 | 0 | 0 | — | 0 | 0 | 0 | 0 | 0 |
| 114 | 5 | 70 | 0 | 0 | — | 10 | 70 | 0 | 0 | 0 |
| 115 | 0 | 0 | 0 | 0 | — | 0 | 0 | 0 | 0 | 0 |
| 116 | 0 | — | 0 | 0 | — | 0 | 0 | 0 | 0 | 0 |
| 117 | 0 | 0 | 0 | 0 | — | 0 | 0 | 0 | 0 | 0 |

TABLE II-continued

PRE-EMERGENCE SCREENING

| COMP. NO. | BRAPP | DIGSA | ECHCG | LOLRI | PANDI | SETFA | SETVI | ALOMY | AVEFA | SORHA |
|---|---|---|---|---|---|---|---|---|---|---|
| 118 | 80 | 100 | 100 | 100 | — | 100 | 100 | 100 | 80 | 100 |
| 119 | 0 | 0 | 0 | 0 | — | 0 | 0 | 0 | 0 | 0 |
| 120 | 20 | 100 | 70 | 30 | — | 60 | 100 | 20 | 20 | 50 |
| 121 | 0 | 0 | 0 | 0 | — | 0 | 0 | 0 | 0 | 0 |
| 122 | 60 | 100 | 80 | 50 | — | 100 | 100 | 70 | 70 | 80 |
| 123 | 0 | 0 | 0 | 0 | — | 0 | 0 | 0 | 0 | 0 |
| 124 | 0 | 100 | 0 | 20 | — | 90 | 100 | 10 | 0 | 30 |
| 125 | 0 | 90 | 0 | 0 | — | 0 | 80 | 0 | 0 | 0 |
| 126 | 10 | 100 | 100 | 0 | — | 70 | 100 | 20 | 20 | 0 |
| 142 | 100 | 100 | 80 | 80 | — | 100 | 100 | 100 | 80 | 100 |

TABLE III

PRE-EMERGENCE SCREENING

| COMP. NO. | ABUTH | AMARE | CHEAL | IPOHE | POROL | XANST | GALAP | CYPES |
|---|---|---|---|---|---|---|---|---|
| 1 | 100 | 100 | 100 | 100 | 100 | 50 | 100 | 75 |
| 2 | 5 | 65 | 40 | 0 | 85 | 0 | — | 5 |
| 3 | 0 | 25 | 0 | 0 | 0 | 0 | — | 0 |
| 4 | 100 | 100 | 100 | 65 | 100 | 20 | 90 | 65 |
| 5 | 40 | 100 | 0 | 10 | 10 | 0 | — | 40 |
| 6 | 100 | 100 | 100 | 40 | 100 | 0 | 90 | 30 |
| 7 | 20 | 100 | 100 | 30 | 100 | 0 | 95 | — |
| 8 | 20 | 100 | 60 | 60 | 100 | 0 | 40 | 25 |
| 9 | 10 | 100 | 35 | 20 | 100 | 0 | — | 10 |
| 10 | 100 | 100 | 100 | 100 | 100 | 15 | — | 75 |
| 11 | 10 | 90 | 30 | 20 | 100 | 0 | — | 5 |
| 12 | 100 | 100 | 80 | 25 | 100 | 0 | — | 40 |
| 13 | 0 | 0 | 0 | 0 | 0 | 0 | 0 | 0 |
| 14 | 50 | 100 | 70 | 15 | 100 | 0 | — | 5 |
| 15 | 0 | 0 | 0 | 0 | 0 | 0 | 0 | 0 |
| 16 | 0 | 0 | 0 | 0 | 0 | 0 | 10 | 0 |
| 17 | 0 | 25 | 5 | 0 | 25 | 0 | — | 0 |
| 18 | 0 | 98 | 20 | 0 | 50 | 0 | — | 0 |
| 19 | 100 | 100 | 100 | 75 | 100 | 15 | 90 | 35 |
| 20 | 50 | 90 | 5 | 15 | 35 | 0 | — | 25 |
| 21 | 25 | 100 | 100 | 20 | 100 | 0 | — | 25 |
| 22 | 0 | 35 | 0 | 0 | 50 | 0 | — | 0 |
| 23 | 15 | 40 | 30 | 20 | 70 | 0 | — | 5 |
| 24 | 5 | 100 | 100 | 65 | 100 | 0 | — | 35 |
| 25 | 100 | 100 | 100 | 80 | 100 | — | — | 60 |
| 26 | 10 | 100 | 100 | 30 | 90 | 0 | — | — |
| 27 | 0 | 100 | 30 | 5 | 90 | 0 | — | 0 |
| 28 | 100 | 100 | 100 | 20 | 100 | 10 | — | — |
| 29 | 100 | 100 | 100 | 70 | 100 | 10 | — | 80 |
| 30 | 100 | 100 | 100 | 70 | 100 | 30 | — | 100 |
| 31 | 0 | 100 | 100 | 0 | 100 | 0 | — | — |
| 32 | 100 | 100 | 100 | 98 | 100 | 5 | — | 70 |
| 33 | 70 | 100 | 100 | 60 | 100 | 0 | — | 30 |
| 34 | 0 | 100 | 100 | 20 | 100 | 0 | — | 0 |
| 35 | 0 | 100 | 90 | 20 | 20 | 0 | — | 0 |
| 36 | 0 | 40 | 0 | 0 | 0 | 0 | — | — |
| 37 | 0 | 80 | 10 | 0 | 0 | 0 | — | — |
| 39 | 0 | 0 | 0 | 0 | 0 | 0 | — | — |
| 40 | 0 | 0 | 0 | 0 | 0 | 0 | — | — |
| 41 | 0 | 50 | 20 | 0 | 0 | 0 | — | 0 |
| 42 | 35 | 93 | 85 | 8 | 100 | 0 | — | 30 |
| 43 | 0 | 90 | 100 | 5 | 95 | 0 | — | 0 |
| 44 | 0 | 0 | 0 | 0 | 0 | 0 | — | 0 |
| 45 | 0 | 100 | 100 | 5 | 100 | 0 | — | 20 |
| 46 | 20 | 98 | 80 | 30 | 100 | 0 | — | — |
| 47 | 0 | 60 | 65 | 10 | 98 | 0 | — | 0 |
| 48 | 0 | 15 | 40 | 0 | 90 | 0 | — | 0 |
| 49 | 0 | 70 | 100 | 20 | 100 | 0 | — | 0 |
| 50 | 0 | 0 | 0 | 0 | 0 | 0 | — | 0 |
| 51 | 0 | 70 | 50 | 0 | 80 | 0 | 20 | 0 |
| 52 | 30 | 100 | 100 | 10 | 100 | 0 | 20 | 20 |
| 53 | 0 | 100 | 90 | 0 | 100 | 0 | 50 | 0 |
| 54 | 0 | 100 | 60 | 0 | 100 | 0 | 20 | 0 |

TABLE III-continued

PRE-EMERGENCE SCREENING

| COMP. NO. | ABUTH | AMARE | CHEAL | IPOHE | POROL | XANST | GALAP | CYPES |
|---|---|---|---|---|---|---|---|---|
| 55 | 10 | 90 | 90 | 2 | 80 | 0 | 30 | 0 |
| 56 | 20 | 100 | 100 | 20 | 100 | 0 | 30 | 20 |
| 57 | 0 | 20 | 0 | 0 | 0 | 0 | 0 | 30 |
| 58 | 0 | 100 | 70 | 0 | 30 | 0 | 50 | 0 |
| 59 | 85 | 98 | 100 | 20 | 100 | 0 | 50 | 0 |
| 60 | 0 | 100 | 30 | 0 | 20 | 0 | 0 | 0 |
| 64 | 0 | 90 | 95 | 0 | 100 | 0 | 0 | 0 |
| 65 | 0 | 70 | 0 | 0 | 20 | 0 | 0 | 0 |
| 66 | 0 | 100 | 100 | 10 | 100 | 0 | 20 | 0 |
| 67 | 0 | 40 | 90 | 0 | 0 | 0 | 0 | 0 |
| 68 | 0 | 0 | 0 | 0 | 0 | 0 | 0 | 0 |
| 70 | 30 | 100 | 100 | 50 | 100 | 0 | 70 | 0 |
| 71 | 0 | 0 | 0 | 0 | 40 | 0 | 30 | 0 |
| 72 | 0 | 0 | 0 | 0 | 0 | 0 | 0 | 0 |
| 73 | 0 | 0 | 0 | 0 | 0 | 0 | 0 | 0 |
| 78 | 0 | 0 | 0 | 0 | 0 | 0 | 0 | 0 |
| 79 | 0 | 0 | 20 | 0 | 0 | 0 | 0 | 0 |
| 80 | 0 | 20 | 40 | 0 | 20 | 0 | 0 | 0 |
| 81 | 20 | 80 | 100 | 40 | 100 | 0 | 60 | 0 |
| 82 | 70 | 98 | 100 | 20 | 100 | 0 | 70 | 0 |
| 83 | 0 | 70 | 70 | 0 | 20 | 0 | 0 | 0 |
| 84 | 50 | 60 | 100 | 0 | 100 | 0 | 40 | 0 |
| 85 | 100 | 100 | 100 | 100 | 100 | 40 | 90 | 50 |
| 86 | 0 | 90 | 100 | 0 | 90 | — | 40 | 0 |
| 87 | 0 | 100 | 70 | 0 | 100 | 0 | 30 | 0 |
| 88 | 0 | 80 | 50 | 0 | 100 | 0 | 90 | 10 |
| 89 | 30 | 100 | 95 | 30 | 100 | 0 | 40 | 30 |
| 90 | 0 | 0 | 0 | 0 | 60 | 0 | — | 0 |
| 91 | 20 | 100 | 80 | 50 | 100 | 0 | 80 | 10 |
| 92 | — | 0 | 0 | 0 | 0 | 0 | 0 | 0 |
| 93 | 20 | 98 | 98 | 40 | 98 | 50 | 80 | 20 |
| 94 | — | 60 | 0 | 0 | 0 | 0 | 40 | 0 |
| 95 | 30 | 0 | 0 | 0 | 0 | 0 | 0 | 0 |
| 96 | 15 | 100 | 100 | 15 | 100 | 0 | 70 | 20 |
| 97 | 0 | 0 | 0 | 0 | 0 | 0 | — | 0 |
| 98 | 5 | 90 | 100 | 10 | 100 | 0 | 40 | 0 |
| 99 | 0 | 35 | 100 | 0 | 50 | 0 | 0 | 0 |
| 100 | 100 | 100 | 100 | 100 | 100 | 20 | 98 | 5 |
| 101 | 100 | 100 | 100 | 60 | 100 | 0 | 75 | 20 |
| 102 | 100 | 100 | 100 | 60 | 100 | 0 | 70 | 0 |
| 103 | 95 | 100 | 100 | 70 | 100 | 5 | 60 | 5 |
| 105 | 20 | 100 | 98 | 30 | 100 | 0 | 85 | 10 |
| 106 | 0 | 95 | 100 | 20 | 90 | 0 | 5 | 0 |
| 107 | 70 | 70 | 100 | 5 | 100 | 0 | 10 | 0 |
| 108 | 100 | 100 | 100 | 100 | 100 | 0 | 90 | 70 |
| 110 | 0 | 95 | 0 | 0 | 40 | 0 | 80 | 10 |
| 111 | 0 | 90 | 0 | 0 | 0 | 0 | 0 | 0 |
| 112 | 0 | 0 | 20 | 0 | 0 | 0 | 0 | 0 |
| 113 | 0 | 20 | 0 | 0 | 0 | 0 | 0 | 0 |
| 114 | 0 | 30 | 20 | 0 | 50 | 0 | 0 | 0 |
| 115 | 0 | 0 | 0 | 0 | 0 | 0 | 0 | 0 |
| 116 | 0 | — | 20 | 0 | 0 | 0 | 0 | — |
| 117 | 0 | 0 | 0 | 0 | 0 | 0 | — | 0 |
| 118 | 100 | 100 | 100 | 100 | 100 | 10 | 70 | 70 |
| 119 | 0 | 40 | 0 | 0 | 0 | 0 | 0 | 0 |
| 120 | 0 | 30 | 90 | 0 | 100 | 0 | 0 | — |
| 121 | 0 | 0 | 0 | 0 | 0 | 0 | 0 | 0 |
| 122 | 0 | 90 | 20 | 5 | 100 | 0 | 100 | 50 |
| 123 | 0 | 40 | 0 | 0 | 0 | 0 | — | 0 |
| 124 | 0 | 90 | 40 | 0 | 100 | 0 | 20 | 0 |
| 125 | 0 | 70 | 0 | 0 | 0 | 0 | 0 | 0 |
| 126 | 0 | 100 | 100 | 0 | 100 | 0 | — | 0 |
| 142 | 100 | 100 | 100 | 60 | 100 | 10 | 95 | 30 |

POST-EMERGENCE HERBICIDAL SCREENING TEST

The soil was prepared with the same methodology described for the pre-emergence test. The following species were used.

The grass weeds planted were "BRAPP"; "ECHCG"; "LOLRI"; "PANDI"; "SETFA"; "SETVI"; "ALOMY"; "AVEFA" and "SORHA".

The broadleaf weeds planted were "ABUTH"; "AMARE"; "CHEAL"; "IPOHE"; "POROL"; "XANST"; "GALAP" and scentless chamomile (*Matricaria perforata*) "MATT". Additionally, "CYPES" nutlets were also sown.

Post-emergence flats were placed in the greenhouse under the same environmental conditions as described for the pre-emergence flats and watered as needed. Plants were grown for 10 to 12 days (or to the appropriate growth stage)

prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 0.25 kg/ha. Treated plants were then returned to a greenhouse and watered daily without wetting the foliage. The degree of weed control was evaluated 17–21 days after application and recorded as percentage of control as compared to the growth of the same species in an untreated control flat of the same age. The percent control scale (0–100%) used to evaluate the pre-emergence treatment was also applied to the post-emergence treatment. The post-emergence screening test results are shown in Table IV (grass weeds) and Table V (broadleaf weeds) below.

TABLE IV

POST EMERGENCE SCREENING

| COMP. NO. | BRAPP | ECHCG | LOLRI | PANDI | SETFA | SETVI | ALOMY | AVEFA | SORHA |
|---|---|---|---|---|---|---|---|---|---|
| 1 | 40 | 75 | 70 | 50 | 85 | 90 | 95 | 90 | 75 |
| 2 | 10 | 0 | 5 | 0 | 5 | 5 | 10 | 0 | 0 |
| 3 | 5 | 0 | 0 | 5 | 10 | 15 | 5 | 0 | 0 |
| 4 | 30 | 15 | 15 | 30 | 65 | 50 | 85 | 75 | 0 |
| 5 | 25 | 5 | 10 | 15 | 25 | 15 | 55 | 50 | 5 |
| 6 | 15 | 20 | 5 | 10 | 20 | 15 | 90 | 50 | 15 |
| 7 | 5 | 0 | 8 | 5 | 10 | 20 | 85 | 10 | 10 |
| 8 | 0 | 5 | 5 | 0 | 15 | 30 | 35 | 10 | 5 |
| 9 | 5 | 5 | 0 | 0 | 0 | 10 | 10 | 5 | 0 |
| 10 | 5 | 10 | 10 | 10 | 10 | 20 | 88 | 60 | 15 |
| 11 | 5 | 0 | 0 | 5 | 0 | 10 | 10 | 8 | 0 |
| 12 | 10 | 35 | 10 | 25 | 10 | 50 | 93 | 50 | 50 |
| 13 | 0 | 0 | 0 | 0 | 0 | 0 | 0 | 0 | 5 |
| 14 | 0 | 0 | 0 | 0 | 0 | 5 | 5 | 0 | 0 |
| 15 | 0 | 0 | 0 | 0 | 0 | 0 | 5 | 0 | 0 |
| 16 | 0 | 0 | 0 | 0 | 0 | 0 | 0 | 5 | 0 |
| 17 | 0 | 0 | 0 | 0 | 0 | 0 | 5 | 0 | 0 |
| 18 | 0 | 0 | 0 | 0 | 0 | 0 | 0 | 0 | 0 |
| 19 | 5 | 20 | 8 | 10 | 0 | 85 | 70 | 65 | 20 |
| 20 | 0 | 0 | 0 | 0 | 0 | 0 | 30 | 15 | 0 |
| 21 | 5 | 0 | 0 | 5 | 5 | 5 | 50 | 25 | 0 |
| 22 | 3 | 15 | 0 | 10 | 5 | 10 | 0 | 0 | 0 |
| 23 | 0 | 5 | 5 | 10 | 15 | 10 | 10 | 0 | 0 |
| 24 | 15 | 70 | 20 | 25 | 75 | 80 | 75 | 55 | 50 |
| 25 | 40 | 65 | 75 | 30 | 90 | 90 | 70 | 65 | 75 |
| 27 | — | 0 | 0 | 8 | 10 | 10 | 15 | 20 | 0 |
| 28 | 10 | 15 | 10 | 15 | 20 | 25 | 75 | 60 | 45 |
| 29 | 5 | 60 | 20 | 15 | 75 | 65 | 90 | 90 | 65 |
| 30 | 60 | 75 | 45 | 60 | 70 | 85 | 90 | 90 | 80 |
| 31 | 5 | 0 | 5 | 15 | 10 | 10 | 20 | 15 | 20 |
| 32 | 75 | 60 | 20 | 30 | 75 | 70 | 90 | 85 | 70 |
| 33 | 0 | 0 | 0 | 5 | 10 | 55 | 40 | 20 | 0 |
| 34 | 5 | 10 | 5 | 5 | 8 | 45 | 60 | 45 | 20 |
| 35 | 0 | 0 | 0 | 0 | 0 | 0 | 0 | 5 | 0 |
| 36 | 0 | 0 | 0 | 0 | 0 | 0 | 0 | 0 | 15 |
| 37 | 0 | 0 | 0 | 0 | 0 | 5 | 0 | 0 | 0 |
| 39 | 0 | 0 | 20 | 0 | 0 | 20 | 0 | 0 | 0 |
| 40 | 0 | 0 | 0 | 0 | 0 | 0 | 20 | 10 | 0 |
| 41 | 0 | 0 | 0 | 0 | 0 | 0 | 0 | 0 | 0 |
| 42 | 30 | 0 | 0 | 20 | 10 | 20 | 70 | 40 | 30 |
| 43 | 0 | 0 | 0 | 20 | 10 | 0 | 40 | 0 | 30 |
| 44 | 0 | 0 | 0 | 0 | 0 | 0 | 0 | 0 | 0 |
| 45 | 5 | 0 | 5 | 5 | 8 | 8 | 40 | 10 | 8 |
| 46 | 5 | 0 | 8 | 10 | 8 | 5 | 20 | 15 | 0 |
| 47 | 5 | 0 | 5 | 8 | 10 | 5 | 5 | 10 | 5 |
| 48 | 3 | 0 | 0 | 5 | 0 | 5 | 5 | 8 | 0 |
| 49 | 5 | 0 | 5 | 10 | 10 | 15 | 10 | 15 | 5 |
| 50 | 0 | 0 | 0 | 0 | 0 | 0 | 0 | 0 | 0 |
| 51 | 10 | 0 | 5 | 5 | 8 | 5 | 5 | 10 | 5 |
| 52 | 8 | 0 | 10 | 10 | 5 | 20 | 20 | 15 | 20 |
| 53 | 10 | 0 | 5 | 10 | 5 | 40 | 10 | 10 | 5 |
| 54 | 5 | 0 | 10 | 5 | 5 | 5 | 5 | 8 | 5 |
| 55 | 5 | 0 | 5 | 10 | 10 | 15 | 10 | 15 | 0 |
| 56 | 5 | 0 | 5 | 10 | 0 | 10 | 25 | 5 | 5 |
| 57 | 10 | 0 | 0 | 5 | 0 | 10 | 0 | 3 | 0 |
| 58 | 0 | 0 | 10 | 10 | 0 | 10 | 10 | 10 | 10 |
| 59 | 10 | 0 | 0 | 0 | 0 | 10 | 60 | 30 | 0 |
| 60 | 5 | 0 | 0 | 0 | 0 | 0 | 0 | 0 | 0 |
| 64 | 0 | 0 | 0 | 40 | 0 | 0 | 0 | 0 | 0 |
| 65 | 15 | 0 | 10 | 10 | 5 | 15 | 15 | 10 | 10 |
| 66 | 10 | 0 | 10 | 25 | 10 | 15 | 10 | 15 | 0 |
| 67 | 0 | 0 | 0 | 0 | 0 | 5 | 0 | 0 | 15 |
| 68 | 5 | 0 | 0 | 0 | 0 | 0 | 0 | 0 | 0 |

TABLE IV-continued

POST EMERGENCE SCREENING

| COMP. NO. | BRAPP | ECHCG | LOLRI | PANDI | SETFA | SETVI | ALOMY | AVEFA | SORHA |
|---|---|---|---|---|---|---|---|---|---|
| 70 | 20 | 5 | 10 | 30 | 5 | 15 | 60 | 50 | 10 |
| 71 | 15 | 0 | 8 | 10 | 0 | 5 | 30 | 65 | 5 |
| 72 | 5 | 0 | 0 | 0 | 0 | 0 | 0 | 0 | 0 |
| 73 | 0 | 0 | 0 | 0 | 0 | 0 | 0 | 0 | 0 |
| 75 | 5 | 5 | 0 | 0 | 0 | 5 | 10 | 0 | 0 |
| 76 | 0 | 5 | 0 | 0 | 0 | 0 | 15 | 0 | 0 |
| 77 | 10 | 0 | 0 | 5 | 5 | 5 | 5 | 0 | 0 |
| 78 | 5 | 0 | 0 | 0 | 0 | 0 | 0 | 0 | 0 |
| 79 | 0 | 0 | 0 | 0 | 0 | 0 | 0 | 0 | 0 |
| 80 | 5 | 0 | 0 | 0 | 5 | 5 | 0 | 0 | 5 |
| 81 | 10 | 0 | 10 | 10 | 10 | 20 | 50 | 35 | 5 |
| 82 | 15 | 0 | 10 | 15 | 15 | 15 | 40 | 15 | 0 |
| 83 | 10 | 0 | 5 | 5 | 5 | 5 | 60 | 30 | 5 |
| 84 | 5 | 0 | 5 | 5 | 5 | 10 | 70 | 75 | 0 |
| 85 | 65 | 85 | 60 | 80 | 60 | 80 | 99 | 100 | 85 |
| 86 | 5 | 10 | 5 | 10 | 20 | 5 | 5 | 10 | 5 |
| 87 | 5 | 10 | 5 | 10 | 15 | 15 | 15 | 20 | 10 |
| 88 | 10 | 10 | 5 | 10 | 10 | 10 | 20 | 5 | 10 |
| 89 | 5 | 10 | 15 | 5 | 20 | 40 | 60 | 35 | 5 |
| 90 | 5 | 10 | 5 | 8 | 10 | 10 | 5 | 0 | 0 |
| 91 | 8 | 10 | 10 | 10 | 15 | 15 | 50 | 40 | 5 |
| 92 | 0 | 0 | 0 | 0 | 0 | 0 | 0 | 0 | 0 |
| 93 | 15 | 20 | 10 | 15 | 20 | 25 | 70 | 50 | 15 |
| 94 | 15 | 0 | 0 | 5 | 15 | 5 | 5 | 0 | 0 |
| 95 | 0 | 0 | 0 | 0 | 0 | 0 | 0 | 0 | 0 |
| 96 | 10 | 0 | 15 | 10 | 10 | 10 | 25 | 20 | 0 |
| 97 | 0 | 0 | 0 | 0 | 0 | 0 | 0 | 0 | 0 |
| 98 | 15 | 5 | 10 | 10 | 10 | 25 | 45 | 65 | 0 |
| 99 | 5 | 0 | 5 | 5 | 0 | 0 | 5 | 0 | 0 |
| 100 | 15 | 60 | 35 | 15 | 70 | 70 | 75 | 85 | 5 |
| 101 | 10 | 60 | 15 | 15 | 25 | 75 | 65 | 75 | 0 |
| 102 | 15 | 10 | 10 | 10 | 5 | 20 | 20 | 35 | 10 |
| 103 | 10 | 30 | 15 | 5 | 5 | 30 | 30 | 25 | 5 |
| 105 | 10 | 0 | 5 | 8 | 0 | 15 | 35 | 15 | 5 |
| 106 | 30 | 0 | 0 | — | 0 | 0 | 10 | 5 | 0 |
| 107 | 10 | 0 | 0 | 0 | 0 | 0 | 10 | 10 | 0 |
| 108 | 30 | 30 | 30 | 70 | 20 | 10 | 90 | 90 | 10 |
| 110 | 10 | 0 | 5 | — | 10 | 5 | 25 | 45 | 0 |
| 111 | 5 | 0 | 0 | — | 10 | 10 | 5 | 0 | 0 |
| 112 | 0 | 0 | 0 | — | 0 | 0 | 0 | 0 | 0 |
| 113 | 0 | 0 | 0 | — | 0 | 0 | 0 | 0 | 0 |
| 114 | 5 | 0 | 0 | — | 10 | 10 | 5 | 10 | 0 |
| 115 | 0 | 0 | 0 | — | 0 | 0 | 0 | 0 | 0 |
| 116 | 0 | 0 | 0 | — | 0 | 0 | 0 | 0 | 0 |
| 117 | 0 | 0 | 0 | — | 0 | 0 | 5 | 0 | 0 |
| 118 | 10 | 15 | 15 | — | 10 | 20 | 90 | 90 | 0 |

TABLE V

POST-EMERGENCE SCREENING

| COMP. NO. | ABUTH | AMARE | CHEAL | IPOHE | POROL | XANST | GALAP | MATIN | CYPE8 |
|---|---|---|---|---|---|---|---|---|---|
| 1 | 60 | 90 | 90 | 60 | 98 | 60 | 90 | 80 | 35 |
| 2 | 15 | 15 | 15 | 20 | 60 | 5 | 30 | 5 | 0 |
| 3 | 0 | 20 | 15 | 0 | 10 | 0 | 30 | 0 | 5 |
| 4 | 15 | 75 | 65 | 65 | 80 | 0 | 95 | 75 | 5 |
| 5 | 10 | 30 | 0 | 30 | 40 | 0 | 100 | 15 | 5 |
| 6 | 20 | 65 | 100 | 80 | 80 | 50 | 100 | 40 | 10 |
| 7 | 10 | 65 | 90 | 55 | 50 | 10 | 98 | 30 | 0 |
| 8 | 10 | 50 | 40 | 50 | 65 | 10 | 50 | 30 | 5 |
| 9 | 10 | 35 | 30 | 60 | 60 | 15 | 35 | 15 | 0 |
| 10 | 10 | 90 | 65 | 65 | 75 | 15 | 95 | 90 | 10 |
| 11 | 5 | 50 | 45 | 25 | 60 | 5 | 99 | 0 | 8 |
| 12 | 30 | 60 | 40 | 35 | 100 | 8 | 98 | 0 | 15 |
| 13 | 0 | 10 | 0 | 5 | 3 | 0 | 3 | 0 | 0 |
| 14 | 10 | 65 | 35 | 40 | 85 | 0 | 85 | 0 | 5 |
| 15 | 0 | 5 | 0 | 0 | 0 | 0 | 0 | 0 | 0 |
| 16 | 0 | 0 | 0 | 5 | 0 | — | 5 | 0 | 0 |
| 17 | 0 | 40 | 50 | 20 | 5 | 10 | 30 | 0 | 0 |

TABLE V-continued

POST-EMERGENCE SCREENING

| COMP. NO. | ABUTH | AMARE | CHEAL | IPOHE | POROL | XANST | GALAP | MATIN | CYPE8 |
|---|---|---|---|---|---|---|---|---|---|
| 18 | 0 | 35 | 5 | 10 | 10 | 0 | 10 | 5 | 0 |
| 19 | 15 | 60 | 70 | 40 | 65 | 10 | 95 | 98 | 0 |
| 20 | 0 | 5 | 0 | 20 | 10 | 0 | 50 | 20 | 0 |
| 21 | 60 | 55 | 50 | 80 | 60 | 5 | 35 | 0 | 5 |
| 22 | 5 | 25 | 40 | 30 | 30 | 0 | 35 | 0 | 0 |
| 23 | 5 | 5 | 20 | 55 | 10 | 3 | 10 | 90 | 0 |
| 24 | 5 | 15 | 95 | 100 | 95 | 60 | 80 | 65 | 5 |
| 25 | 65 | 100 | 85 | 88 | 88 | 15 | 90 | 65 | 15 |
| 27 | 20 | 60 | 70 | 30 | 85 | 15 | 15 | 10 | 10 |
| 28 | 30 | 65 | 100 | 60 | 98 | 35 | 100 | 40 | 5 |
| 29 | 60 | 25 | 100 | 70 | 98 | 35 | 100 | 80 | 5 |
| 30 | 30 | 80 | 95 | 75 | 100 | 35 | 100 | 100 | 5 |
| 31 | 15 | 50 | 100 | 55 | 85 | 40 | 60 | 0 | 10 |
| 32 | 40 | 35 | 100 | 60 | 95 | 40 | 100 | 95 | 15 |
| 33 | 10 | 40 | 50 | 70 | 90 | 0 | 65 | 50 | 0 |
| 34 | 25 | 60 | 85 | 65 | 95 | 40 | 60 | 5 | 5 |
| 35 | 0 | 8 | 15 | 60 | 70 | 3 | 25 | 5 | 0 |
| 36 | 0 | 5 | 10 | 15 | 50 | 0 | 5 | 5 | 0 |
| 37 | 0 | 5 | 10 | 35 | 15 | 0 | 10 | 5 | 0 |
| 39 | 0 | 0 | 0 | 0 | 20 | 0 | — | 0 | 0 |
| 40 | 0 | 0 | 0 | 0 | 0 | 10 | — | 0 | 0 |
| 41 | 0 | 10 | 0 | 10 | 30 | 0 | — | 0 | 0 |
| 42 | 30 | 80 | 40 | 60 | 85 | 30 | — | 0 | 0 |
| 43 | 30 | 70 | 90 | 50 | 90 | 30 | — | 20 | 10 |
| 44 | 0 | 0 | 5 | 15 | 15 | 0 | — | 3 | 0 |
| 45 | 10 | 60 | 50 | 55 | 35 | 30 | — | 5 | 0 |
| 46 | 5 | 50 | 15 | 30 | 55 | 5 | — | 10 | 0 |
| 47 | 20 | 70 | 60 | 50 | 85 | 10 | — | 20 | 0 |
| 48 | 5 | 60 | 45 | 40 | 45 | 35 | — | 5 | 0 |
| 49 | 60 | 70 | 85 | 55 | 95 | 60 | — | 10 | 5 |
| 50 | 0 | 0 | 3 | 8 | 10 | 3 | — | 0 | 0 |
| 51 | 40 | 60 | 50 | 15 | 70 | 10 | — | 5 | 10 |
| 52 | 45 | 50 | 100 | 60 | 90 | 35 | — | 5 | 10 |
| 53 | 35 | 50 | 85 | 55 | 85 | 5 | — | 5 | 10 |
| 54 | 10 | 70 | 55 | 15 | 95 | 5 | — | 5 | 8 |
| 55 | 30 | 40 | 25 | 50 | 75 | 5 | — | 5 | 10 |
| 56 | 30 | 75 | 50 | 50 | 90 | 15 | — | 5 | 10 |
| 57 | 3 | 10 | 0 | 5 | 8 | 0 | — | 5 | 0 |
| 58 | 15 | 50 | 35 | 60 | 85 | 10 | — | 0 | 10 |
| 59 | 0 | 30 | 90 | 60 | 50 | 30 | 30 | 40 | 10 |
| 60 | 8 | 50 | 15 | 60 | 40 | 0 | 15 | 8 | 0 |
| 64 | 20 | 20 | 40 | 70 | 30 | 5 | 40 | 30 | 0 |
| 65 | 25 | 80 | 100 | 85 | 80 | 40 | 50 | 25 | 5 |
| 66 | 10 | 85 | 100 | 90 | 95 | 25 | 60 | 5 | 15 |
| 67 | 0 | 20 | 20 | 30 | 60 | 10 | 10 | 5 | 0 |
| 68 | 0 | 30 | 10 | 15 | 25 | 10 | 15 | 0 | 0 |
| 70 | 55 | 65 | 100 | 85 | 85 | 30 | 80 | 75 | 10 |
| 71 | 5 | 10 | 5 | 30 | 25 | 0 | 50 | 10 | 0 |
| 72 | 5 | 15 | 20 | 10 | 15 | 0 | 10 | 0 | 5 |
| 73 | 0 | 5 | 5 | 5 | 0 | 0 | 10 | 0 | 0 |
| 75 | 15 | 10 | 20 | 15 | 15 | 0 | 25 | 10 | 0 |
| 76 | 0 | 15 | 10 | 10 | 5 | 0 | 35 | 20 | 0 |
| 77 | 10 | 25 | 5 | 15 | 35 | 5 | 25 | 5 | 0 |
| 78 | 20 | 15 | 15 | 15 | 15 | 0 | 5 | 0 | 0 |
| 79 | 0 | 0 | 0 | 5 | 0 | 0 | 5 | 0 | 0 |
| 80 | 10 | 8 | 30 | 20 | 50 | 0 | 25 | 5 | 5 |
| 81 | 55 | 65 | 65 | 75 | 90 | 40 | 35 | 15 | 15 |
| 82 | 70 | 80 | 95 | 25 | 65 | 25 | 75 | 40 | 20 |
| 83 | 25 | 5 | 75 | 60 | 30 | 10 | 40 | 30 | 5 |
| 84 | 45 | 40 | 75 | 50 | 85 | 20 | 70 | 60 | 5 |
| 85 | 80 | 75 | 100 | 70 | 90 | 40 | 95 | 100 | 15 |
| 86 | 35 | 65 | 95 | 65 | 40 | 20 | 55 | 70 | 10 |
| 87 | 25 | 75 | 90 | 40 | 70 | 20 | 55 | 80 | 15 |
| 88 | 15 | 40 | 35 | 15 | 60 | 0 | 50 | 0 | 5 |
| 89 | 10 | 70 | 95 | 30 | 90 | 25 | 85 | 25 | 15 |
| 90 | 10 | 65 | 50 | 10 | 25 | 15 | 25 | 70 | 5 |
| 91 | 15 | 80 | 100 | 60 | 90 | 30 | 70 | 50 | 10 |
| 92 | 0 | 5 | 5 | 15 | 10 | 0 | 5 | — | 0 |
| 93 | 70 | 100 | 95 | 70 | 90 | 50 | 40 | — | 20 |
| 94 | 0 | 40 | 10 | 20 | 15 | 0 | 5 | — | 0 |
| 95 | 15 | 0 | 0 | 0 | 0 | 0 | 0 | — | 0 |
| 96 | 50 | 55 | 60 | 60 | 90 | 20 | 55 | 40 | 15 |
| 97 | 0 | 0 | 10 | 0 | 0 | 0 | 10 | 0 | 0 |
| 98 | 60 | 100 | 75 | 15 | 85 | 15 | 60 | — | 15 |

TABLE V-continued

POST-EMERGENCE SCREENING

| COMP. NO. | ABUTH | AMARE | CHEAL | IPOHE | POROL | XANST | GALAP | MATIN | CYPE8 |
|---|---|---|---|---|---|---|---|---|---|
| 99 | 0 | 45 | 35 | 20 | 40 | 10 | 40 | 0 | 0 |
| 100 | 85 | 88 | 90 | 50 | 95 | 35 | 80 | 98 | 0 |
| 101 | 100 | 100 | 70 | 65 | 90 | 25 | 75 | 40 | 10 |
| 102 | 35 | 88 | 80 | 100 | 80 | 25 | 65 | 95 | 10 |
| 103 | 75 | 80 | 100 | 80 | 95 | 30 | 65 | 50 | 10 |
| 105 | 40 | 80 | 60 | 60 | 65 | 40 | 100 | 30 | 10 |
| 106 | 5 | 40 | 70 | 80 | 50 | 50 | 30 | — | 0 |
| 107 | 5 | 50 | 70 | 70 | 40 | 10 | 50 | — | 0 |
| 108 | 50 | 70 | 40 | 80 | 70 | 10 | 90 | — | 0 |
| 110 | 10 | 40 | 5 | 5 | 50 | 0 | 20 | — | 5 |
| 111 | 5 | 20 | 10 | 20 | 20 | 0 | 5 | — | 5 |
| 112 | 0 | 0 | 0 | 0 | 0 | 0 | 0 | — | 0 |
| 113 | 0 | 65 | 15 | 5 | 20 | 0 | 10 | — | 0 |
| 114 | 15 | 50 | 10 | 25 | 30 | 0 | 10 | — | 0 |
| 115 | 0 | 0 | 0 | 0 | 5 | 0 | 0 | — | 0 |
| 116 | 0 | 5 | 0 | 5 | 40 | 0 | 10 | — | 0 |
| 117 | 0 | 0 | 0 | 0 | 0 | 0 | 0 | — | 0 |
| 118 | 60 | 100 | 100 | 40 | 100 | 15 | 100 | — | 10 |
| 142 | 5 | 80 | 100 | 45 | 60 | 15 | 80 | — | — |

POST FLOODING POST EMERGENCE HERBICIDAL SCREENING TEST

Seeds of three weeds species were seeded into 8.9×8.9 cm pots. The pots were previously filled with clay soil which contained 2.2% organic matter and had a pH of 5.7. The weed species were *Echinochloa crus-galli* ("ECHCG"); *Cyperus serotinus* ("CYPDr"); and *Sagittaria pygmaea* ("SAGPY"). In addition, the rice hybrid "Kosihikara" (*Oryza saliva*) was also seeded.

The pots were placed into a 10 liter plastic tubs, lined with a plastic bag. At an early growth stage, the rice plants were transplanted into an 8.9 cm×8.9 cm pot, 3 plants per pot at a depth of 2 cm. The pots were placed into the tubs with the weed species. The tubs were flooded with water to a depth of 2–3 cm.

At a middle growth stage the tubs were injected with the test material in acetone at a rate of 0.25 kg per hectare. The degree of weed control was evaluated and recorded 22 days after treatment as a percentage of weed control as compared to the growth of the same species of the same age in an untreated control flat. Percent control is the total injury to the plants due to all factors including: inhibited emergence, stunting, malformation, albinism, chlorosis and other types of plant injury. The control ratings range from 0 to 100 percent, where 0 represents no effect with growth equal to the untreated control and where 100 represents complete kill. The symbol "—" indicates that no test was performed at the 0.25 kg/ha level of application. Representative results of the inventive compounds are shown in Table VI.

TABLE VI

POST FLOODING POST EMERGENCE

| COMP. NO. | ECHCG | CYPDI | SAGPY |
|---|---|---|---|
| 1 | 100 | 100 | 90 |
| 6 | 90 | 100 | 70 |
| 12 | 10 | 35 | 0 |
| 24 | 98 | 95 | 60 |
| 32 | 100 | — | 80 |
| 46 | 70 | 40 | 50 |
| 85 | 100 | 100 | 90 |
| 100 | 100 | 100 | 50 |
| 101 | 90 | 100 | 60 |
| 142 | 85 | 100 | 85 |
| 118 | 75 | 100 | 90 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A method for controlling undesirable vegetation comprising applying to an area where control is desired an herbicidally effective amount of a compound of formula (Ia),

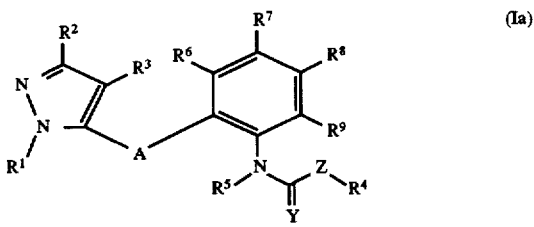

(Ia)

wherein:

$R^1$ is optionally substituted $C_1$–$C_6$ alkyl or $C_1$–$C_6$ haloalkyl;

$R^2$ is optionally substituted $C_1$–$C_6$ alkyl, $C_1$–$C_6$ haloalkyl or $C_3$–$C_6$ cycloalkyl;

$R^3$ is hydrogen, halogen, $C_1$–$C_6$ alkyl or $C_1$–$C_6$ haloalkyl;

$R^4$ is optionally substituted $C_1$–$C_6$ alkyl, $C_1$–$C_6$ haloalkyl, optionally substituted $C_1$–$C_6$ alkoxy, optionally substituted $C_3$–$C_6$ cycloalkyl, optionally substituted ($C_1$–$C_6$) alkoxy($C_1$–$C_6$)alkyl, optionally substituted $C_2$–$C_6$ alkenyl, optionally substituted $C_2$–$C_6$ alkynyl, optionally substituted aryl, optionally substituted heteroaryl, or an optionally substituted five or six membered heterocyclic ring containing one or more heteroatoms selected from O, N or S;

$R^5$ is hydrogen, optionally substituted $C_1$–$C_6$ alkyl or ($C_1$–$C_6$)alkoxy-($C_1$–$C_6$)alkyl;

$R^6$, $R^7$, $R^8$ and $R^9$ are independently selected from hydrogen, halogen, optionally substituted $C_1$–$C_6$ alkyl, optionally substituted $C_2$–$C_6$ alkenyl, optionally substituted $C_2$–$C_6$ alkynyl, optionally substituted $C_1$–$C_6$ alkoxy, ($C_1$–$C_6$)alkoxy-($C_1$–$C_6$)alkyl, $C_1$–$C_6$ haloalkyl, $C_1$–$C_6$ haloalkoxy, cyano, nitro, —S(O)$_p$—$R^{10}$ wherein p is 0, 1 or 2 and $R^{10}$ is $C_1$–$C_3$ alkyl or $C_1$–$C_3$ haloalkyl, —OSO$_2$$R^{11}$ wherein $R^{11}$ is $C_1$–$C_3$ alkyl, —CO$_2$H, —COR$^{12}$, —COOR$^{12}$ or —NHCOR$^{12}$ wherein $R^{12}$ is $C_1$–$C_6$ alkyl, $C_1$–$C_6$ haloalkyl, optionally substituted $C_3$–$C_6$ cycloalkyl, optionally substituted aryl, optionally substituted heteroaryl, ($C_1$–$C_6$) alkoxy-($C_1$–$C_6$)alkyl or $C_1$–$C_6$ alkylthio, —CONR$^{13}$R$^{14}$ or —NR$^{13}$R$^{14}$ wherein $R^{13}$ and $R^{14}$ may be the same or different and are each hydrogen, $C_1$–$C_6$ alkyl, $C_1$–$C_6$ haloalkyl, optionally substituted $C_3$–$C_6$ cycloalkyl, optionally substituted $C_2$–$C_6$ alkenyl, optionally substituted $C_2$–$C_6$ alkynyl, optionally substituted aryl, optionally substituted heteroaryl, ($C_1$–$C_6$)alkoxy-($C_1$–$C_6$)alkyl or $C_1$–$C_6$ alkylthio, or $R^{13}$ and $R^{14}$ together with the N to which they are bound may form a ring having 3–8 members, one or more of which may be O, S or N; and A is O, S, SO or SO$_2$;

Y is O or S;

Z is O;

or an agriculturally acceptable salt thereof.

2. A method for controlling undesirable vegetation according to claim 1, wherein: $R^1$ is $C_1$–$C_3$ alkyl or $C_1$–$C_3$ haloalkyl; $R^2$ is $C_1$–$C_3$ alkyl or $C_1$–$C_3$ haloalkyl; $R^3$ is hydrogen; and $R^5$ is hydrogen.

3. A method for controlling undesirable vegetation according to claim 1, wherein $R^1$ is methyl; $R^2$ is trifluoromethyl; $R^3$ is hydrogen; $R^4$ is isopropyl; $R^5$ is hydrogen; $R^6$ is hydrogen; $R^7$ is methyl; $R^8$ is hydrogen; $R^9$ is hydrogen and Z is O.

4. A method for controlling undesirable vegetation according to claim 1, wherein $R^1$ is methyl; $R^2$ is trifluoromethyl; $R^3$ is hydrogen; $R^4$ is ethyl; $R^5$ is hydrogen; $R^6$ is hydrogen; $R^7$ is methyl; $R^8$ is hydrogen; $R^9$ is hydrogen and Z is O.

* * * * *